United States Patent [19]
Sugai et al.

[11] Patent Number: 5,817,810
[45] Date of Patent: Oct. 6, 1998

[54] TRYPTANTHRINE COMPOUNDS

[75] Inventors: Fumio Sugai; Syunichi Matsumoto; Nobuko Akiba; Yukimasa Watanabe; Hirofumi Kawaguchi; Sakae Saitoh, all of Osaka, Japan

[73] Assignee: Mita Industrial Co., Ltd., Osaka, Japan

[21] Appl. No.: 685,608

[22] Filed: Jul. 24, 1996

[30] Foreign Application Priority Data

| Jul. 26, 1995 | [JP] | Japan | 7-190530 |
| Jul. 26, 1995 | [JP] | Japan | 7-190531 |
| Nov. 6, 1995 | [JP] | Japan | 7-287464 |
| May 29, 1996 | [JP] | Japan | 8-135566 |

[51] Int. Cl.$^6$ ............................................. C07D 471/04
[52] U.S. Cl. ................................... 544/246; 430/78
[58] Field of Search ........................................ 544/246

[56] References Cited

U.S. PATENT DOCUMENTS

| 4,666,526 | 5/1987 | Rolf et al. | 544/246 |
| 5,117,706 | 6/1992 | Kojima | 430/58 |
| 5,420,255 | 5/1995 | Guentner et al. | 534/655 |
| 5,441,955 | 8/1995 | Baker et al. | 544/246 |
| 5,616,441 | 4/1997 | Kawaguchi et al. | 544/246 |

FOREIGN PATENT DOCUMENTS

| 0513558 | 4/1992 | European Pat. Off. . |
| 281050 | 6/1928 | Germany . |
| 95/13807 | 5/1995 | WIPO . |

OTHER PUBLICATIONS

Bergman, *Tetrahedron*, 41 p2883–4 (1985).
Suzuki et al, *Chemical Abstracts*, vol. 121, No. 241713 (1994).
Organic Photoreceptors for Imaging Systems, Paul Borsenberger et al. pp. 189–211.

*Primary Examiner*—Emily Bernhardt
*Attorney, Agent, or Firm*—Beveridge, DeGrandi, Weilacher & Young, L.L.P.

[57] ABSTRACT

The present invention provides a novel tryptanthrine derivative represented by a general formula:

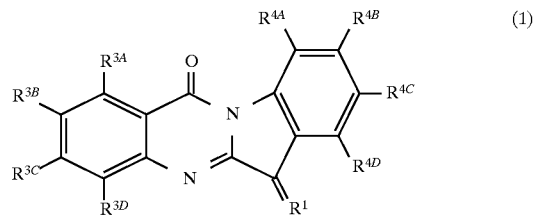

(1)

wherein $R^1$ is an oxygen atom, or group represented by a formula:

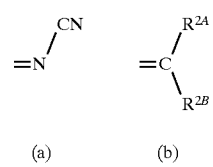

(a) (b)

wherein $R^{2A}$ and $R^{2B}$ are the same or different and indicate a hydrogen atom, a cyano group, an acyl group, an alkoxycarbonyl group or an alkyl group, provided that $R^{2A}$ and $R^{2B}$ are not hydrogen atoms simultaneously; and $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent, provided that when $R^1$ is an oxygen atom, any one of $R^{3A}$ through $R^{4D}$ is a cyano group.

Such a tryptanthrine derivative has an excellent electron transport capability to be suitably used for the electrophotosensitive material.

3 Claims, 6 Drawing Sheets

TRYPTANTHRINE COMPOUNDS

BACKGROUND OF THE INVENTION

The present invention relates to a novel tryptanthrine derivative and an electrophotosensitive material for use in image forming apparatuses such as electrostatic copying machines, laser-beam printers, plain paper facsimiles and the like.

In the above image forming apparatuses, so-called organic photoconductors (OPC) are widely used, which comprise an electric charge generating material which generates an electric charge due to light irradiation, an electric charge transport material for transporting the electric charge thus generated, and a binder resin providing a layer wherein these materials are dispersed.

The organic photoconductors are roughly classified into an electrophotosensitive material comprising a single-layer type photosensitive layer containing therein the electric charge generating material together with the electric charge transport material, and an electrophotosensitive material comprising a multi-layer type photosensitive layer wherein an electric charge generating layer containing the electric charge generating material and an electric charge transport layer containing the electric charge transport material are laminated. Of these, the multi-layer type photosensitive layer are normally used. In the above multi-layer type photosensitive layer, an electric charge transport layer which has a greater thickness than an electric charge generating layer is typically disposed at the outside of the electrophotosensitive material in the light of mechanical strength.

Known electric charge transport materials for use in such electrophotosensitive materials include a hole transport type and an electron transport type. Of these electric charge transport materials, many of those having higher carrier mobility which can impart a practicable photosensitivity to the electrophotosensitive materials are the hole transport type. Accordingly, in the electrophotosensitive materials presently put into practice, the multi-layer type wherein the electric charge transport layer is disposed at the outside of the photosensitive layer are negative-charge type.

The electrophotosensitive material comprising the aforesaid multi-layer type photosensitive layer of negative charge must be charged by negative corona discharge which entails generation of a large amount of ozone. Ozone causes environmental contamination or deterioration of the electrophotosensitive material.

In order to solve the above problems, there has been had development and study of an electron transport material having high carrier mobility. For example, Japanese Laid-Open Patent Publication No.1-206349 (1989) has proposed the use of a compound having a diphenoquinone structure as the electron transport material.

Diphenoquinones, in general, have poor compatibility with resin binder, failing to be dispersed uniformly. Therefore, hopping distance of electron is increased and electron movement particularly in a low electric field is dull. Although the diphenoquinones have high carrier mobility, when they are used as the electron transport material of the electrophotosensitive materials, they cannot satisfactorily exhibit their inherent characteristics. This leads to an increase in residual potential of the electrophotosensitive materials, resulting in insufficient photosensitivity.

As described above, many of the electrophotosensitive materials presently put into practice have the multi-layer type photosensitive layer. On the other hand, the electrophotosensitive materials having the single-layer type photosensitive layer have simple structure and are easy to manufacture, and they also have several advantages in avoiding damage in coating of the layer and in improving the optical characteristics.

Additionally, the single-layer type photosensitive layer can be used in both the positive charge type and the negative charge type by employing, for example, the electron transport material and the hole transport material as the electric charge transport material. There may be a possibility to broaden the applicability. The diphenoquinones, however, inhibit the transport of electron and hole due to mutual interaction with the hole transport material. For this reason, the electrophotosensitive material having the single-layer type photosensitive layer which contains the diphenoquinone has not been widely put to practical use.

SUMMARY OF THE INVENTION

It is a primary object of this invention to provide a novel compound suitably used as the electron transport material in the electrophotosensitive material and the like.

It is another object of this invention to provide an electrophotosensitive material which presents a higher photosensitivity than the conventional ones.

The present inventors have had extensive investigation to solve the above problems, and it is found that tryptanthrine represented by the following formula (2), known as a pigment intermediate, has a broader $\pi$ electron conjugated system to present a greater electron transport capability than conventional diphenoquinone compounds.

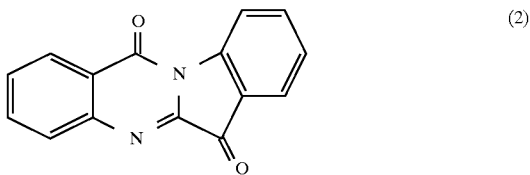

(2)

Then, consideration has been given to discover a compound suitably used as the electron transport material in which this tryptanthrine (2) is used as a basic skeleton, and they have accomplished a tryptanthrine derivative of this invention represented by the following general formula (1):

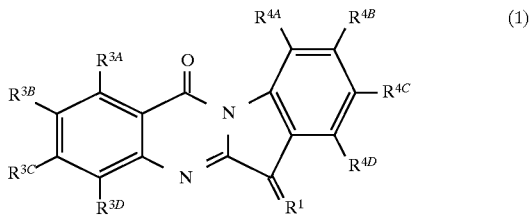

(1)

wherein $R^1$ indicates an oxygen atom, a group represented by a formula (a):

(a)

or a group represented by a general formula (b):

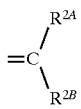

wherein $R^{2A}$ and $R^{2B}$ are the same or different and indicate a hydrogen atom, a cyano group, an acyl group, an alkoxycarbonyl group or an alkyl group, provided that $R^{2A}$ and $R^{2B}$ are not hydrogen atoms simultaneously,
wherein when $R^1$ is an oxygen atom, any one of $R^{3A}$, $R^{3B}$, $R^{3C}$, $R^{3D}$, $R^{4A}$, $R^{4B}$, $R^{4C}$ and $R^{4D}$ is a cyano group while the others are the same or different and indicate a hydrogen atom or an alkyl group which may have a substituent; and
when $R^1$ is a group of the formula (a) or of the general formula (b), $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent.

The tryptanthrine derivative (1) of this invention presents a greater electron transport capability than the conventional diphenoquinones and a good matching with the electric charge generating material (pigment), thus enabling to smoothly inject electron from the electric charge generating material. In addition, the tryptanthrine derivative (1) has a good solvent solubility and compatibility with the resin binder and is uniformly dispersed in the photosensitive layer, thereby reducing a hopping distance of electron to exhibit an excellent electron transport characteristics especially in a low electric field. Hence, the tryptanthrine derivative (1) of this invention provides an excellent function as the electron transport material for use in the electrophotosensitive material.

Due to good electron transport capability, the tryptanthrine derivative (1) of this invention is also applicable to solar batteries, electroluminescent devices and the like.

The tryptantrine derivative (1) of this invention contains the following compounds represented by the general formulas:

General formula (11):

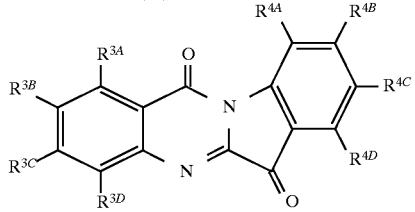

wherein any one of $R^{3A}$, $R^{3B}$, $R^{3C}$, $R^{3D}$, $R^{4A}$, $R^{4B}$, $R^{4C}$ and $R^{4D}$ is a cyano group while the others are the same or different and indicate a hydrogen atom or an alkyl group which may have a substituent.

General formula (12):

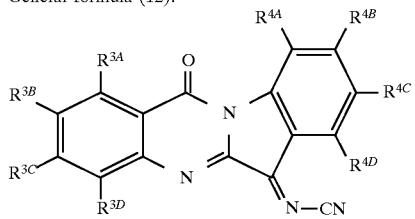

wherein $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent.

General formula (13):

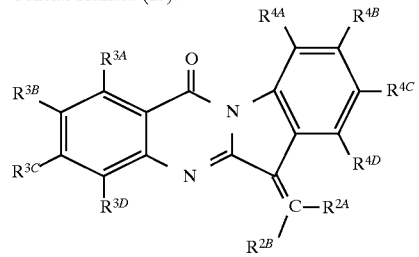

wherein $R^{2A}$ and $R^{2B}$ are the same or different and indicate a hydrogen atom, a cyano group, an acyl group, an alkoxycarbonyl group or an alkyl group, provided that $R^{2A}$ and $R^{2B}$ are not hydrogen atoms simultaneously, $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent.

An electrophotosensitive material of this invention comprises a conductive substrate and a photosensitive layer provided thereon, which contains the tryptanthrine derivative (1) of this invention. Therefore, it has a high photosensitivity.

More specifically, the photosensitive layer containing the aforesaid tryptanthrine derivative (1) is excellent in electron transporting in a low electric field and also reduces the rate of recombination between electron and hole in the photosensitive layer. As a result, an apparent charge generation efficiency approaches an actual value, resulting in high photosensitivity. Additionally, the residual potential of the photosensitive material is lowered, so that stability and durability during repetitive exposure are improved.

Preferred organic photosensitive layers used in this invention include:

a single-layer type photosensitive layer comprising a resin binder, an electric charge generating material, the tryptanthrine derivative (1) which serves as the electron transport material, and a hole transport material; and a multi-layer type photosensitive layer comprising an electric charge generating layer containing an electric charge generating material and an electric charge transport layer containing a resin binder and the tryptanthrine derivative (1) serving as the electron transport material.

Since the tryptanthrine derivative (1) causes no mutual interaction with the hole transport material, which inhibits the transport of electron and hole. Therefore, it is possible to prepare an electrophotosensitive material having still higher photosensitivity when used in the single-layer type photosensitive layer in which the hole transport material and the tryptanthrine derivative (1).

As the electric charge generating material, a phthalocyanine pigment or a perylene pigment is suitable. As the hole transport material, a benzidine derivative is suitable.

In the electrophotosensitive material of this invention, the organic photosensitive layer may further include an electron acceptive compound having a redox potential of from −0.8 to −1.4 V. The electron acceptive compound serves to take electron from the electric charge generating material and deliveries the electron to the tryptanthrine derivative (1). This allows the electron to be injected even more smoothly from the electric charge generating material to the tryptanthrine derivative (1). Hence, the resultant electrophotosensitive material has further improved photosensitivity.

DETAILED DESCRIPTION OF THE INVENTION

Figure 1:
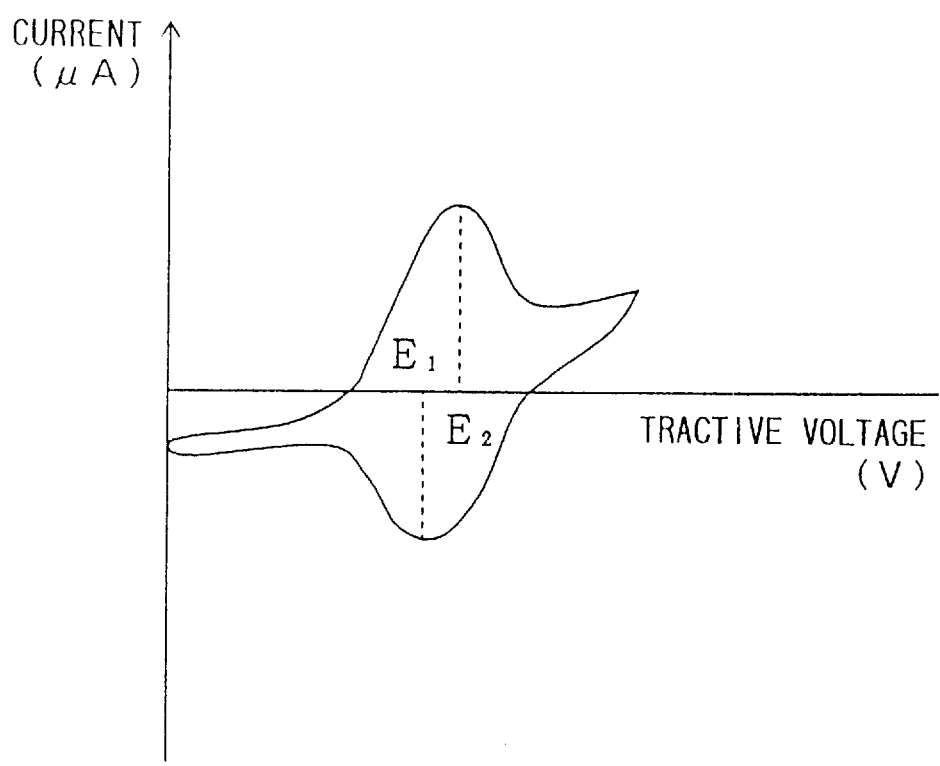
FIG. 1 is a graph illustrating the relationship between the tractive voltage (V) and the current (μA) for obtaining the redox potential of the electron acceptive compound.

Following description is given on the tryptanthrine derivative (11), which belongs to the tryptanthrine derivative (1), represented by the formula:

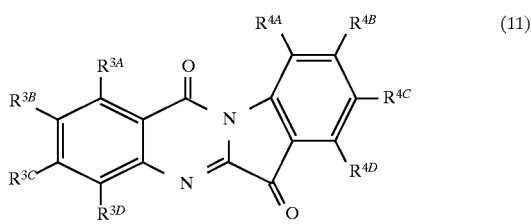

wherein any one of $R^{3A}$, $R^{3B}$, $R^{3C}$, $R^{3D}$, $R^{4A}$, $R^{4B}$, $R^{4C}$ and $R^{4D}$ is a cyano group; and the others are the same or different and indicate a hydrogen atom or an alkyl group which may have a substituent.

By the function of the cyano group substituted at a tryptanthrine ring, the tryptanthrine derivative (11) has a higher electron acceptability, solvent solubility and compatibility with the resin binder, than the tryptanthrine (2).

In the tryptanthrine derivative (11), either of the rings at both ends of the tryptanthrine ring is substituted with only one cyano group. If the respective end rings are substituted with a cyano group, or if either of the end rings is substituted with two or more cyano groups, the solvent solubility and the compatibility with the resin binder deteriorate.

Most suitably used as the tryptanthrine derivative (11), due to simple structure, is a compound wherein only one cyano group is substituted with either of the rings at both ends of the tryptanthrine ring, and the others have no substituent, as described above. Specifically, any one of $R^{3A}$, $R^{3B}$, $R^{3C}$, $R^{3D}$, $R^{4A}$, $R^{4B}$, $R^{4C}$ and $R^{4D}$ is a cyano group, and the others are all hydrogen atoms. Either or both of the end rings of the tryptanthrine ring may be substituted with one or more alkyl groups which may have a substituent. Such as tryptanthrine derivative (11) is further improved in solvent solubility and compatibility with resin binder.

Examples of the aforesaid alkyl group include alkyl groups having 1 to 6 carbon atoms such as methyl, ethyl, n-propyl, isopropyl, n-butyl, isobutyl, sec-butyl, tert-butyl, pentyl and hexyl.

Examples of the substituent with which the alkyl group may be substituted include halogen atoms such as fluorine, chlorine, bromine, iodine and the like; aryl groups such as phenyl, tolyl, xylyl, biphenylyl, o-terphenyl, naphthyl, anthryl, phenanthryl and the like; alkoxy groups such as methoxy, ethoxy, n-propoxy, isopropoxy, n-butoxy, isobutoxy, sec-butoxy, tert-butoxy, pentyloxy and hexyloxy; and acyl groups such as acetyl, propionyl, butyryl, isobutyryl, valeryl, isovaleryl, pivaloyl, benzoyl, 2-naphthoyl and o-toluoyl.

In order to synthesize a compound wherein $R^{4C}$ is a cyano group, which belongs to the tryptanthrine derivative (11), for example, an isato acid anhydride derivative represented by a general formula (1a) is reacted with a bromoisatine derivative represented by a general formula (1b) in a suitable solvent in the presence of a base or the like, to obtain a bromine compound of the tryptanthrine derivative represented by a general formula (1c).

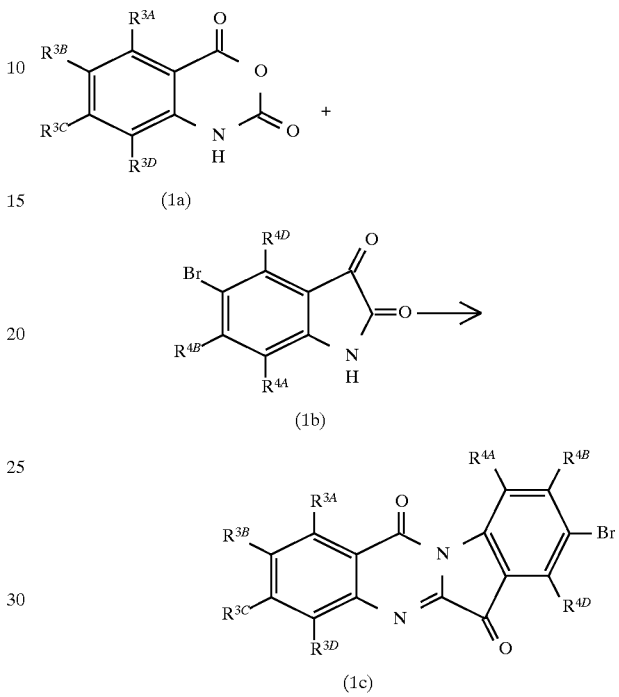

wherein $R^{3A}$, $R^{3B}$, $R^{3C}$, $R^{3D}$, $R^{4A}$, $R^{4B}$ and $R^{4D}$ are as defined above.

The resultant bromine compound (1c) is reacted with a copper cyanide or the like in a suitable solvent to substitute the bromine with a cyano group, to synthesize the titled compound.

Examples of the solvent used for the preceding reaction include toluene and pyridine which also function as a base, among others. When toluene or the like which does not function as a base is used as the solvent, 1,4-diazabicyclo[2,2,2]octane or the like is employed as the base. The reaction is performed at a reflux temperature for 2 to 6 hours.

Examples of the solvent used for the succeeding reaction include N-methylpyrrolidone and hexamethylphosphorictriamido. The reaction is performed at temperatures of from 170° to 180° C. for 3 to 6 hours.

To synthesize a compound wherein any one of $R^{4A}$, $R^{4B}$ and $R^{4D}$ except for $R^{4C}$ is a cyano group, which belongs to the tryptanthrine derivative (11), a bromoisatine derivative wherein a bromine is substituted at a corresponding position is used instead of the bromoisatine derivative (1b).

To synthesize a compound wherein any one of $R^{3A}$, $R^{3B}$, $R^{3C}$ and $R^{3D}$ is a cyano group, which belongs to the tryptanthrine derivative (11), a bromoisato acid anhydride derivative of the aforesaid general formula (1a) wherein a bromine is substituted at a corresponding position is reacted with an unbromized-isatine derivative in a similar manner as described above.

Exemplified compounds of the tryptanthrine derivative (11) include a compound represented by the following formula:

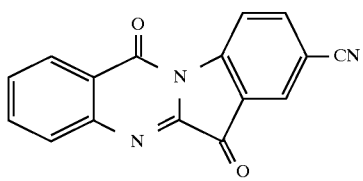
(11-1)

The following description is given on a tryptanthrine derivative represented by the aforesaid general formula (12):

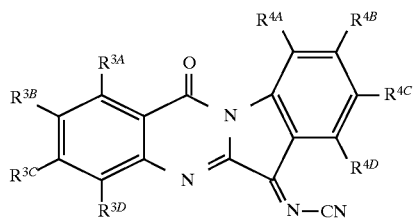
(12)

wherein $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent.

In such a tryptanthrine derivative (12), one of the carbonyl groups of the tryptanthrine ring is substituted with the group of the aforesaid formula (a), which functions to improve the electron acceptability as well as the solvent solubility and the compatibility with resin binder, than the tryptanthrine derivative (2).

Examples of the alkyl group with which the aforesaid tryptanthrine derivative (12) may be substituted, and examples of the substituent with which the alkyl group may be substituted, include the same as mentioned above respectively.

It is desirable that in the above tryptanthrine derivative (12), the number of the alkyl groups substituted at both the end rings of the tryptanthrine ring is 1 to 4. By the function of the alkyl group, the solvent solubility and the compatibility with resin binder are further improved.

Examples of such tryptanthrine derivative (12) include the following compounds:

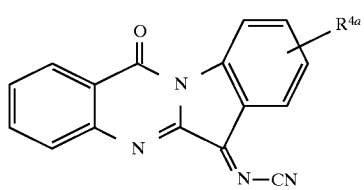
(12a)

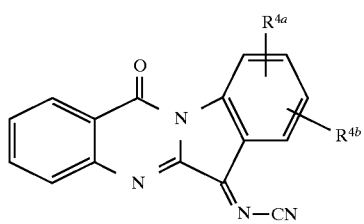
(12b)

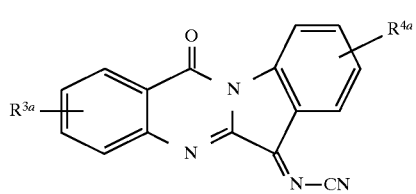
(12c)

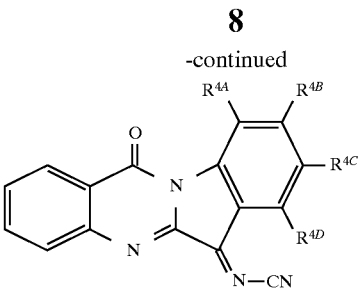
(12d)

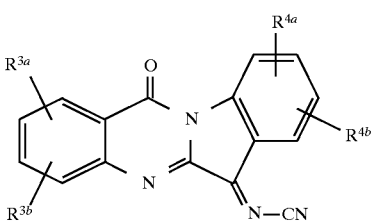
(12e)

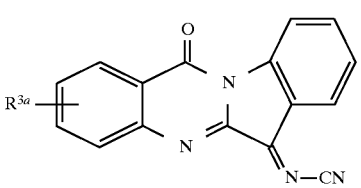
(12f)

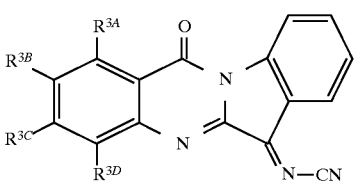
(12g)

wherein $R^{3A}$, $R^{3B}$, $R^{3C}$, $R^{3D}$, $R^{4A}$, $R^{4B}$, $R^{4C}$, $R^{4D}$, $R^{3a}$, $R^{3b}$, $R^{4a}$ and $R^{4b}$ are the same or different and indicate an alkyl group which may have a substituent.

To synthesize the tryptanthrine derivative (12), the aforesaid isato acid anhydride derivative (1a) is reacted with an isatine derivative represented by a general formula (1d) in a suitable solvent to synthesize a tryptanthrine derivative represented by a general formula (1e).

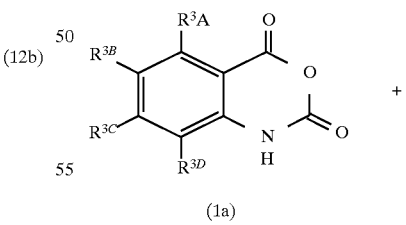
(1a)

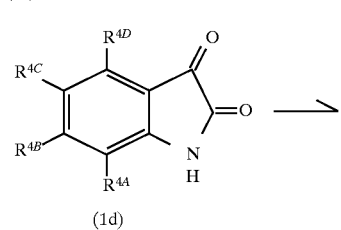
(1d)

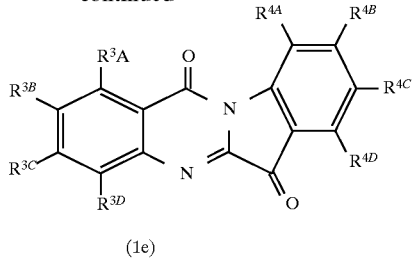

(1e)

wherein $R^{3A}$, $R^{3B}$, $R^{3C}$, $R^{3D}$, $R^{4A}$, $R^{4B}$, $R^{4C}$ and $R^{4D}$ are as defined above.

The resultant derivative (1e) is reacted with bistrimethylsilyl carbodiimido in a suitable solvent under an inert atmosphere such as of argon, nitride or the like, to synthesize the tryptanthrine derivative (12).

The conditions of the preceding reaction are as defined above.

Examples of the solvent used for the succeeding reaction include methylene chloride, chloroform, tetrahydrofuran, dimethylformamido and dimethylsulfoxide. The reaction is performed at temperatures of from 20° to 30° C. for about 10 to 15 hours.

Exemplified compounds of the tryptanthrine derivative (12) include a compound, which belongs to the compound of the aforesaid general formula (12a), represented by the following formula:

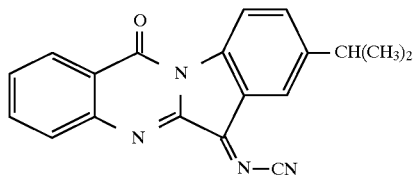

(12a-1)

The following description is given on a tryptanthrine derivative represented by the general formula (13):

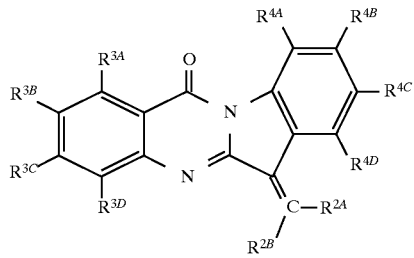

(13)

wherein $R^{2A}$ and $R^{2B}$ are the same or different and indicate a hydrogen atom, a cyano group, an acyl group, an alkoxylcarbonyl group or an alkyl group, provided that $R^{2A}$ and $R^{2B}$ are not hydrogen atoms simultaneously; and $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group which may have a substituent.

In such a tryptanthrine derivative (13), one of the carbonyl groups of the tryptanthrine ring is substituted with the group of the general formula (b), which functions to improve the electron acceptability as well as the solvent solubility and the compatibility with resin binder, than the tryptanthrine (2).

In the aforesaid tryptanthrine derivative (13), examples of the alkyl group which may be substituted on the both end rings of the tryptanthrine ring, and examples of the substituent with which the alkyl group may be substituted, include the same as mentioned above respectively.

Examples of the alkyl group and acyl group corresponding to $R^{2A}$ and $R^{2B}$ of the group (b), respectively, include the same as those aforementioned.

Examples of the alkoxycarbonyl group include methoxycarbonyl, ethoxycarbonyl, n-propoxycarbonyl, isopropoxycarbonyl, tert-butoxycarbonyl, pentyloxycarbonyl and hexyloxycarbonyl.

To synthesize the tryptanthrine derivative (13), the isato acid anhydride derivative (1a) is reacted with isatine derivative (1d) to give the tryptanthrine derivative (1e). The derivative (1e) is reacted with a diethylphosphonate derivative represented by the following general formula (1f):

(1f)

wherein $R^{2A}$ and $R^{2B}$ are as defined above, in a suitable solvent in the presence of sodium hydride or the like to synthesize the tryptanthrine derivative (13).

Examples of the solvent used for the above reaction include tetrahydrofuran and dimethylformamido. The reaction is performed at 0° to 25° C. for about 1 to 24 hours.

A tryptanthrine derivative (13) wherein both $R^{2A}$ and $R^{2B}$ are cyano groups is synthesized by reacting the aforesaid tryptanthrine derivative (1e) with malononitrile in a suitable solvent in the presence of sodium ethoxide or the like.

Examples of the solvent used for the reaction include tetrahydrofuran, ethanol and pyridine. The reaction is performed at 25° to 100° C. for about 2 to 5 hours.

Exemplified compounds of the tryptanthrine derivative (13) include compounds represented by the following formulas:

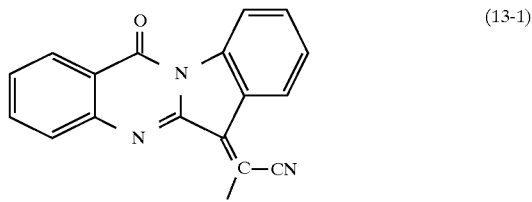

(13-1)

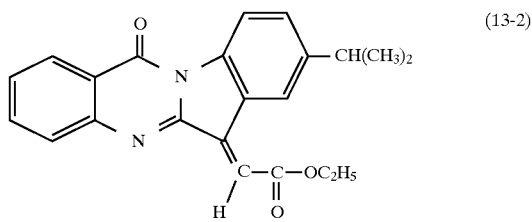

(13-2)

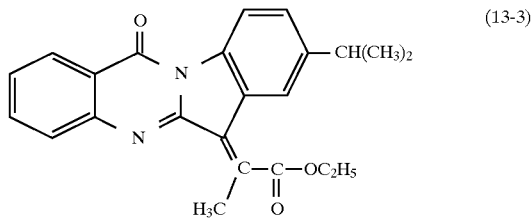

(13-3)

The electrophotosensitive material according to this invention comprises a conductive substrate and a photosensitive layer provided thereon, which contains one or more tryptanthrine derivatives of this invention represented by the general formula (1) as the electron transport material.

As described above, the photosensitive layer includes the single-layer type and the multi-layer type. The single-layer type photosensitive layer comprises the tryptanthrine derivative (1) of this invention serving as the electron transport material, a hole transport material and an electric charge generating material, all of which are dispersed in a resin binder. The electrophotosensitive material having the single-layer type photosensitive layer is applicable to both the positive charge type and the negative charge type, however, the positive charge type is preferred because it does not employ negative corona discharge.

The multi-layer type electrophotosensitive material comprises an electric charge generating layer containing an electric charge generating material and an electric charge transport layer containing the tryptanthrine derivative (1) of this invention, which serves as the electron transport material. The electrophotosensitive material having the multi-layer type photosensitive layer is applicable to both the positive charge type and negative charge type electrophotosensitive materials depending upon the lamination order of the layers. For the same reason as described, it is desirable to be used as the positive charge type in which the electric charge transport layer is the outer layer.

Although the structure of this invention is applicable to both the single-layer type and the multi-layer type, the single-layer type is preferred because the structure of this invention is applicable to both the positive charge type and the negative charge type, as describe above, and because the structure of the single-layer type electrophotosensitive material is simple and its manufacture is easy. Thus, there are advantages that it is possible to prevent such damage in coating that occurs in forming a layer by applying a solution on a previously formed layer, and optical characteristics is improved due to less interface between layers.

In the electrophotosensitive material comprising the single-layer type photosensitive layer of positive charge, an electron (−) emitted from the electric charge generating material in the process of exposure are smoothly injected into the tryptanthrine derivative (1), and transported to the surface of the photosensitive layer by giving and receiving of electron between the tryptanthrine derivative (1), thereby canceling the positive charge (+) on the surface of the photosensitive layer which has previously been applied.

On the other hand, a hole (+) is injected into the hole transport material and transported to the conductive substrate by giving and receiving of hole between the hole transport material, so that the positive charge is canceled by the negative charge (−) which has previously been applied to the conductive substrate.

It assume that since the tryptanthrine derivative (1) and the hole transport material do not interact with each other during this process, as described above, the hole (+) and the electron (−) are efficiently and smoothly transported without forming trap in the course, thereby increasing the photosensitivity of the electrophotosensitive material.

As mentioned above, it is desirable to employ an electron acceptive compound having a redox potential of from −0.8 to −1.4 V, together with the tryptanthrine derivative (1).

The aforesaid electron acceptive compound has a lower energy level of LUMO (Lowest Unoccupied Molecular Orbital) than that of the electric charge generating material, and therefore, it acts to take electron from the electric charge generating material when a pair of electron and hole is generated by the electric charge generating material by means of light irradiation. This eliminates a rate of loss of the electron and the hole due to their recombination in the electric charge generating material, and increases efficiency of electric charge generation.

The aforesaid electron acceptive compound also serves to efficiently transport the electron thus taken from the electric charge generating material to the tryptanthrine derivative (1) serving as the electron transport material. Accordingly, when the electron acceptive compound and the tryptanthrine derivative (1) are jointly used, the electron generated by the electric charge generating material can be smoothly transported, resulting in further improved photosensitivity.

The redox potential of the electron acceptive compound is limited to the above range for the following reasons.

The electron acceptive compound whose redox potential is below −0.8 V, lowers the level of an electron traveling while alternating between trap and detrap to a level at which detrapping is unattainable, so that carrier trap is formed to inhibit the transport of the electron, thereby lowing the photosensitivity of the electrophotosensitive material.

Conversely, an electron acceptive compound whose redox potential exceeds −1.4 V has a higher energy level of LUMO than the electric charge generating material. Therefore, it does not serve to take electron from the electric charge generating material during the generation of a pair of electron and hole, failing to increase the efficiency of the electric charge generation. This leads to a decrease of the photosensitivity of the electrophotosensitive material.

In terms of the photosensitivity of the electrophotosensitive material, the most suitable redox potential of the electron acceptive compound is in the range of from −0.85 to −1.00 V.

The redox potential is measured by means of a three-electrode system cyclic voltametry using the following materials.

Electrode: work electrode (glassy carbon electrode)
counter electrode (platinum electrode)

Reference electrode: silver nitrate electrode (0.1N AgNo$_3$-CH$_3$CN solution)

Measurement solution:
Electrolyte: perchlorate tetra-n-butylammonium (0.1 mol)
Subject substance: electron acceptive compound (0.001 mol)
Solvent: CH$_2$Cl$_2$ (1 liter)

The measurement solution is prepared by mixing the above ingredients.

As shown in FIG. 1, the relationship between index voltage (V) and current ($\mu$A) is found, and the values of $E_1$ and $E_2$ indicated in the figure are determined to calculate a redox potential by the following equation:

$$\text{Redox potential} = (E_1 + E_2)/2 \text{ (V)}$$

The electron acceptive compounds are not particularly limited as long as such compounds have the electron acceptability and a redox potential of from 0.8 to −1.4 V.

Such electron acceptive compounds may be selected from the group consisting of benzoquinone compounds, naphthoquinone compounds, anthraquinone compounds, diphenoquinone compounds, malononitril compounds, thiopyran compounds, 2,4,8-trinitrothioxanthone, fluorenone compounds including 3,4,5,7-tetranitro-9-fluorenone, dinitroanthracene, dinitroacridine, nitroanthraquinone, dinitroanthraquinone, among others.

Most suitably used are benzoquinone compounds represented by a general formula (EA1):

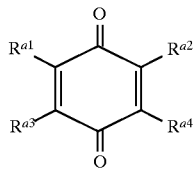
(EA1)

wherein $R^{a1}$, $R^{a2}$, $R^{a3}$ and $R^{a4}$ are the same or different and indicate a hydrogen atom, an alkyl group, an alkoxy group, an aryl group, an aralkyl group, a cycloalkyl group or an amino group which may have a substituent; and compounds which belongs to a diphenoquinone compound, represented by the general formula (EA2):

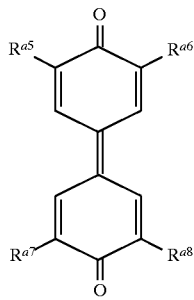
(EA2)

wherein $R^{a5}$, $R^{a6}$, $R^{a7}$ and $R^{a8}$ are the same or different and indicate a hydrogen atom, an alkyl group, an alkoxy group, an aryl group, an aralkyl group, a cycloalkyl group or an amino group which may have a substituent.

Example of the alkyl group, alkoxy group and phenyl group in the above formulas include the same as mentioned above respectively.

Examples of the aralkyl group include benzyl, benzhydyl, trityl and phenethyl.

Examples of the cycloalkyl group include cycloalkyl groups having 3 to 6 carbon atoms such as cyclopropyl, cyclobutyl, cyclopentyl and cyclohexyl.

Examples of the amino group which may have a substituent include amino, monomethylamino, dimethylamino, monoethylamino and diethylamino.

Examples of the benzoquinone compound include p-benzoquinone (redox potential: −0.81 V) represented by a formula (EA1-1) and 2,6-di t-butyl-p-benzoquinone (redox potential: −1.31 V) represented by a formula (EA1-2).

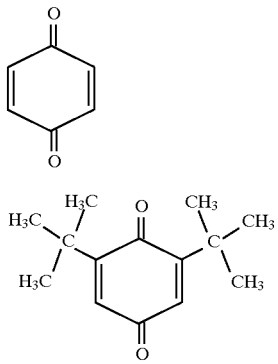
(EA1-1)

(EA1-2)

Examples of the diphenoquinone compound include 3,5-dimethyl-3',5'-di-tert-butyl-4,4'-diphenoquinone (redox potential: −0.86 V) represented by the formula (EA2-1) and 3,5,3',5'-tetrakis(t-butyl)-4,4'-diphenoquinone (redoxpotential: −0.94 V) represented by the formula (EA2-2).

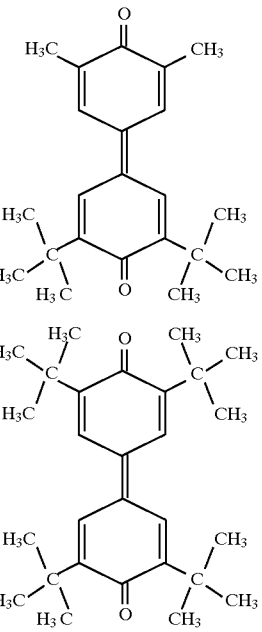
(EA2-1)

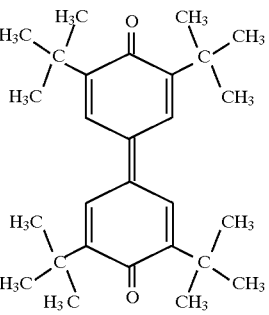
(EA2-2)

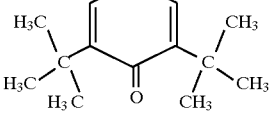

These electron acceptive compounds may be used alone or in any combination thereof.

The following description is given on various ingredients used for the electrophotosensitive materials of this invention.

Hole Transport Material

Examples of the hole transport material include compounds represented by the following general formulas (HT1) through (HT13):

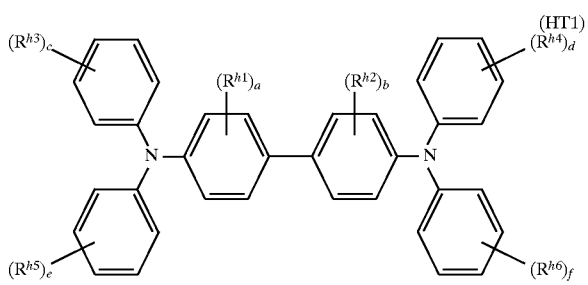
(HT1)

wherein $R^{h1}$, $R^{h2}$, $R^{h3}$, $R^{h4}$, $R^{h5}$ and $R^{h6}$ are the same or different and indicate a hydrogen atom, a halogen atom, an alkyl group which may have a substituent, an alkoxy group which may have a substituent or an aryl group which may have a substituent; a and b are the same or different and indicate an integer of 1 to 4; c, d, e and f are the same or different and indicate an integer of 1 to 5; and when a is more than 2, each $R^{h1}$ may differ from one another, and the same is true for $R^{h2}$, $R^{h3}$, $R^{h4}$, $R^{h5}$ or $R^{h6}$.

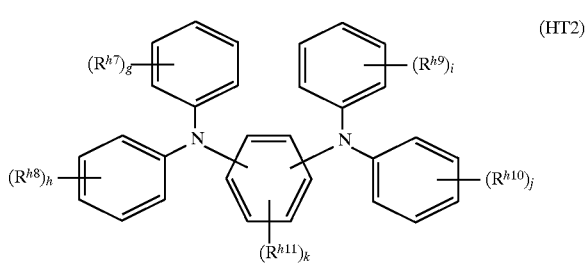
(HT2)

wherein $R^{h7}$, $R^{h8}$, $R^{h9}$, $R^{h10}$ and $R^{11}$ are the same or different and indicate a hydrogen atom, a halogen atom, an alkyl group which may have a substituent, an alkoxy group which may have a substituent or an aryl group which may have a substituent; g, h, i and j are the same or different and indicate an integer of 1 to 5; k indicates an integer of 1 to 4; and when g is more than 2, each $R^{h7}$ may differ from one another, and the same is true for $R^{h8}$, $R^{h9}$, $R^{h10}$ or $R^{h11}$.

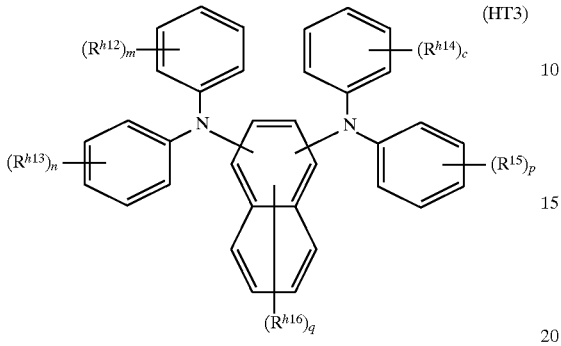

(HT3)

wherein $R^{h12}$, $R^{h13}$, $R^{h14}$ and $R^{h15}$ are the same or different and indicate a hydrogen atom, a halogen atom, an alkyl group which may have a substituent, an alkoxy group which may have a substituent or an aryl group which may have a substituent; $R^{h16}$ indicate a hydrogen atom, a halogen atom, a cyano group, a nitro group, an alkyl group which may have a substituent, an alkoxy group which may have a substituent or an aryl group which may have a substituent; m, n, o and p are the same or different and indicate an integer of 1 to 5; q indicates an integer of 1 to 6; and when m is more than 2, each $R^{h12}$ may differ from one another, and the same is true for $R^{h13}$, $R^{h14}$, $R^{h15}$ or $R^{h16}$.

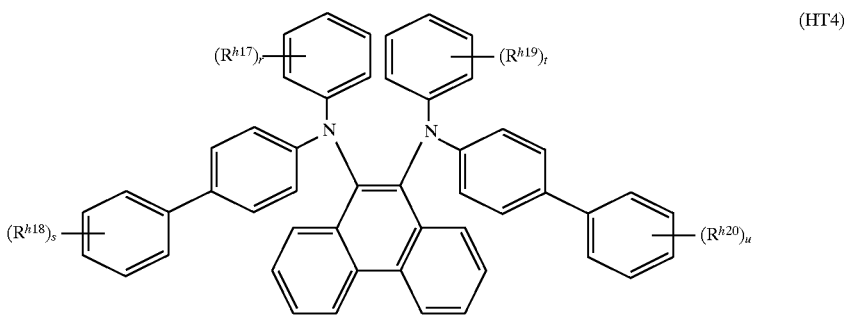

(HT4)

wherein $R^{h17}$, $R^{h18}$, $R^{h19}$ and $R^{h20}$ are the same or different and indicate a hydrogen atom, a halogen atom, an alkyl group which may have a substituent, an alkoxy group which may have a substituent or an aryl group which may have a substituent; r, s, t, and u are the same or different and indicate an integer of 1 to 5; and when r is more than 2, each $R^{h17}$ may differ from one another, and the same is true for $R^{h18}$, $R^{h19}$ or $R^{h20}$.

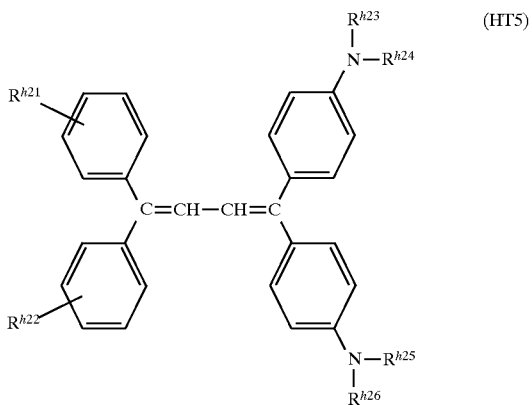

(HT5)

wherein $R^{h21}$ and $R^{h22}$ are the same or different and indicate a hydrogen atom, a halogen atom, an alkyl group or an alkoxy group; and $R^{h23}$, $R^{h24}$, $R^{h25}$ and $R^{h26}$ are the same or different and indicate a hydrogen atom, an alkyl group or an aryl group.

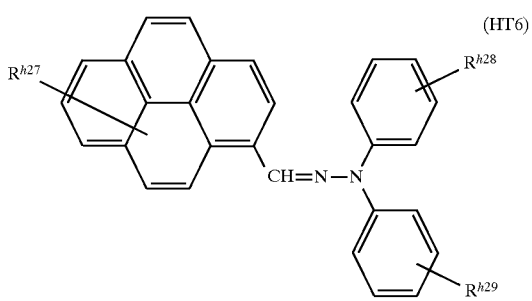

(HT6)

wherein $R^{h27}$, $R^{h28}$ and $R^{h29}$ are the same or different and indicate a hydrogen atom, a halogen atom, an alkyl group or an alkoxy group.

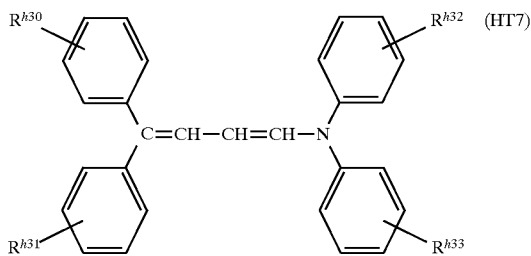
(HT7)

wherein $R^{h30}$, $R^{h31}$, $R^{h32}$ and $R^{h33}$ are the same or different and indicate a hydrogen atom, a halogen atom, an alkyl group or an alkoxy group.

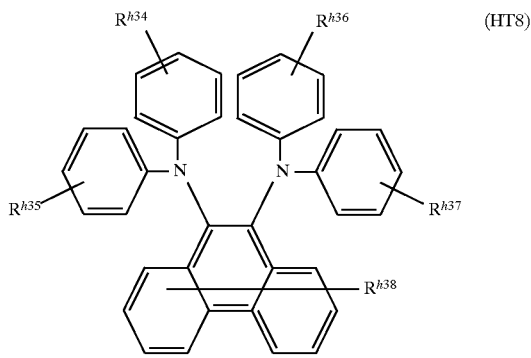
(HT8)

wherein $R^{h34}$, $R^{h35}$, $R^{h36}$, $R^{h37}$ and $R^{h38}$ are the same or different and indicate a hydrogen atom, a halogen atom, an alkyl group or an alkoxy group.

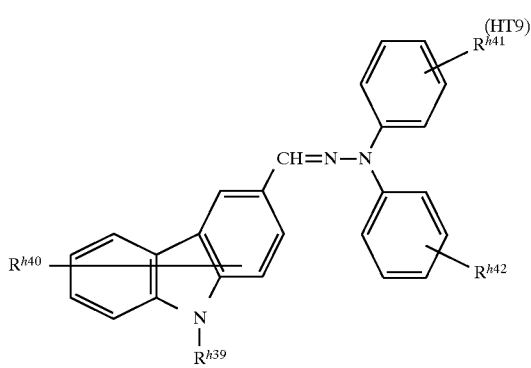
(HT9)

wherein $R^{h39}$ indicates a hydrogen atom or an alkyl group; and $R^{h40}$, $R^{h41}$ and $R^{h42}$ are the same or different and indicate a hydrogen atom, a halogen atom, an alkyl group or an alkoxy group.

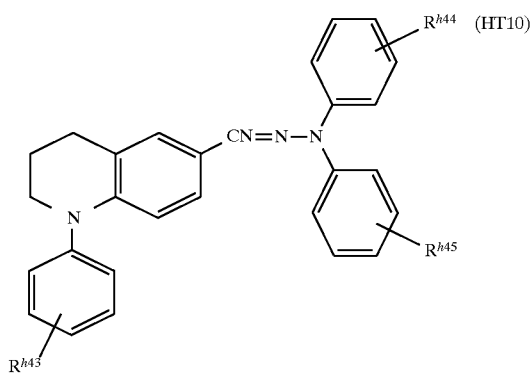
(HT10)

wherein $R^{h43}$, $R^{h44}$ and $R^{h45}$ are the same or different and indicate a hydrogen atom, a halogen atom, an alkyl group or an alkoxy group.

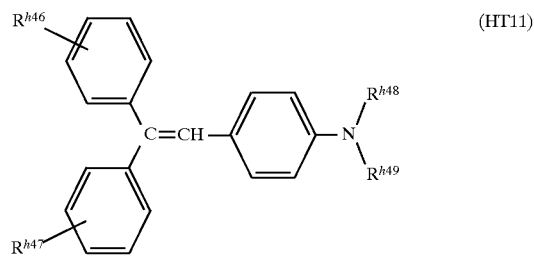
(HT11)

wherein $R^{h46}$ and $R^{h47}$ are the same or different and indicate a hydrogen atom, a halogen atom, an alkyl group which may have a substituent or an alkoxy group which may have a substituent; and $R^{h48}$ and $R^{h49}$ are the same or different and indicate a hydrogen atom, an alkyl group which may have a substituent or an aryl group which may have a substituent.

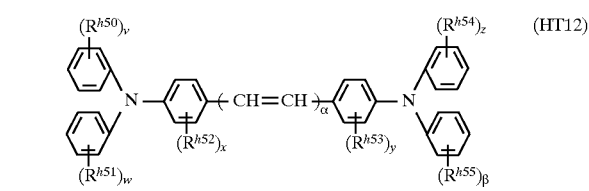
(HT12)

wherein $R^{h50}$, $R^{h51}$, $R^{h52}$, $R^{h53}$, $R^{h54}$ and $R^{h55}$ are the same or different and indicate a hydrogen atom, an alkyl group which may have a substituent, an alkoxy group which may have a substituent or an aryl group which may have a substituent; α indicates an integer of 1 to 10; and v, w, x, y, z and β are the same or different and indicate an integer of 1 or 2; and when v is 2, each $R^{h50}$ may differ from each other, and the same is true for $R^{h51}$, $R^{h52}$, $R^{h53}$, $R^{h54}$ or $R^{h55}$.

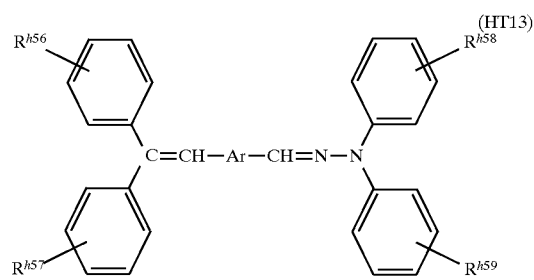
(HT13)

wherein $R^{h56}$, $R^{h57}$, $R^{h58}$ and $R^{h59}$ are the same or different and indicate a hydrogen atom, a halogen atom, an alkyl group or an alkoxy group; and Ar indicates a group Ar1, Ar2 or Ar3, represented by the following formulas:

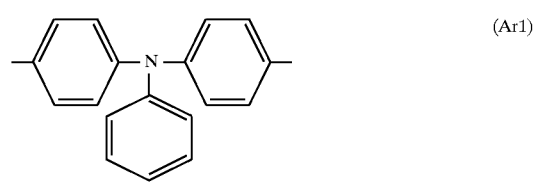
(Ar1)

(Ar2)

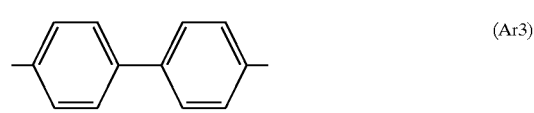
(Ar3)

In the hole transport materials as exemplified above, examples of the alkyl group, the alkoxy group, the aryl group and the halogen atom include the same as described respectively.

Examples of the substituent with which the above groups may be substituted include halogen atom, amino group, hydroxyl group, carboxyl group which may be esterified, cyano group, alkyl group having 1 to 6 carbon atoms, alkoxy group having 1 to 6 carbon atoms, and alkenyl group having 2 to 6 carbon atoms which may have an aryl group. A position at which the aforesaid substituent is substituted is not particularly limited.

In this invention, beside the conventional hole transport materials as mentioned above, there may be used conventional hole transport materials, for example, oxadiazole compounds such as 2,5-di(4-methylaminophenyl)-1,3,4-oxadiazole; styryl compounds such as 9-(4-diethylaminostyryl)anthracene; carbazole compounds such as polyvinylcarbazole; organic polysilane compounds; pyrazoline compounds such as 1-phenyl-3-(p-dimethylaminophenyl)pyrazoline; hydrazone compounds; triphenylamine compounds; nitrogen containing cyclic compounds such as indole compounds, oxazole compounds, isoxazole compounds, thiazole compounds, thiadiazole compounds, imidazole compounds, pyrazole compounds and triazole compounds; condensed polycyclic compounds, among others.

In this invention, a mixture of one or more hole transport materials may be used. When the hole transport material having film forming properties (e.g., polyvinylcarbazole) is used, a resin binder is not necessarily needed.

Of the aforementioned hole transport materials, such compounds as having ionization potential (Ip) of from 4.8 to 5.6 eV are preferred in this invention, particularly those having mobility of greater than $1 \times 10^{-6}$ cm$^2$/V·sec in field strength of $3 \times 10^5$ V/cm are more preferred.

By the use of the hole transport material having the ionization potential of within the aforesaid range, the residual potential is further reduced, thereby increasing the photosensitivity. Although the reason for this is not clear, it appears that:

The ease of injection of hole from the electric charge generating material into the hole transport material is closely related to the ionization potential of the hole transport material. If the ionization potential of the hole transport material exceeds the aforesaid range, less holes are injected from the electric charge generating material into the hole transport material, or the degree of receiving and transporting of hole between the hole transport material is lowered, thus leading to decrease in photosensitivity.

In a system where the hole transport material and electron transport material coexist, it is necessary to avoid the interaction between the both, that is, the formation of an electric charge moving complex. If such a complex is formed, the recombination of hole and electron occurs, thereby reducing the mobility of the electric charge. If the ionization potential of the hole transport material is below the aforesaid range, it is liable to form the complex between the hole transport material and the electron transport material to cause the above recombination. As a result, the apparent quantum yield decreases, leading to a poor photosensitivity.

Examples of the hole transport material to be suitably used in this invention include a compound, which belongs to the benzidine derivative of the aforesaid general formula (HT1), represented by the formula (HT1-1):

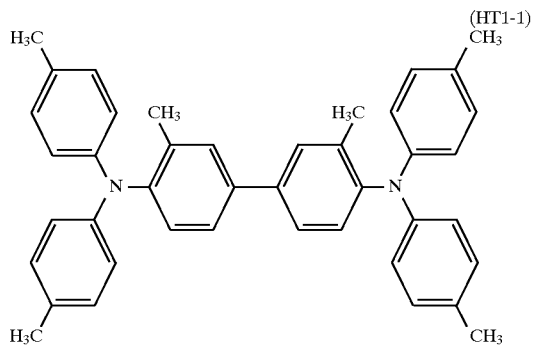

(HT1-1)

Electric Charge Generating Material

Examples of the electric charge generating material include compounds represented by the following general formulas (CG1) through (CG12): (CG1) Metal-free phthalocyanine (CG1) Metal-free phthalocyanine

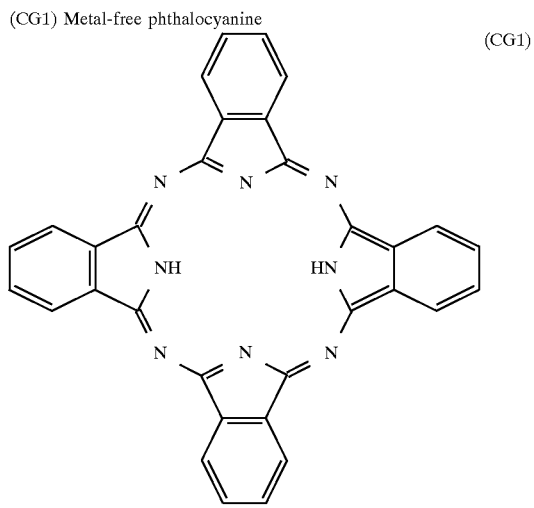

(CG1)

(CG2) Oxotitanyl phthalocyanine

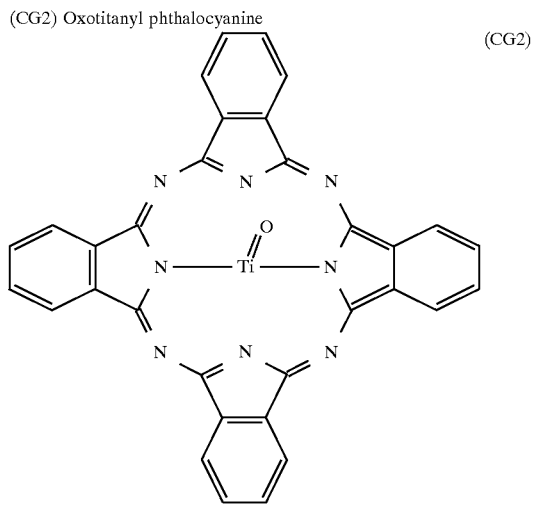

(CG2)

-continued (CG3) Perylene pigment

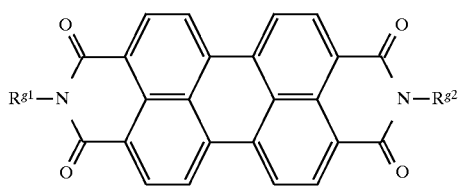
(CG3)

wherein $R^{g1}$ and $R^{g2}$ are the same or different and indicate a substituted or an unsubstituted alkyl group having 18 or less carbon atoms, a cycloalkyl group, an aryl group, an alkanoyl group or an aralkyl group; (CG4) Bisazo pigment $$A^1-N=N-X-N=N-A^2 \quad (CG4)$$

wherein $A^1$ and $A^2$ are the same or different and indicate a coupler residue; and X indicates:

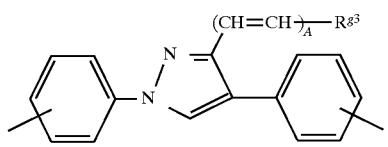

wherein $R^{g3}$ indicates a hydrogen atom, an alkyl group, an aryl group or a heterocyclic group, the alkyl group, aryl group and heterocyclic group which may have a substituent; and A is 0 or

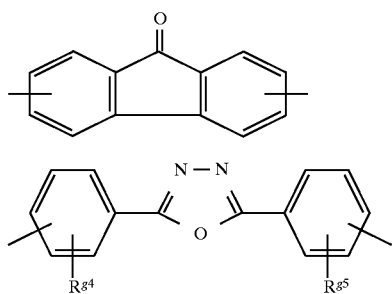

wherein $R^{g4}$ and $R^{g5}$ are the same or different and indicate a hydrogen atom, an alkyl group having 1 to 5 carbon atoms, a halogen atom, an alkoxy group, an aryl group or an aralkyl group;

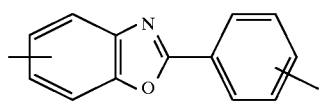

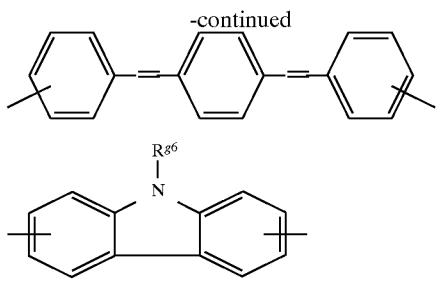

wherein $R^{g6}$ indicates a hydrogen atom, an ethyl group, a chloroethyl group or a hydroxyethyl group;

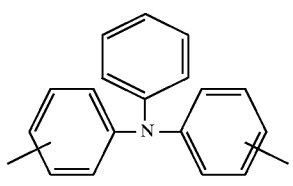

or

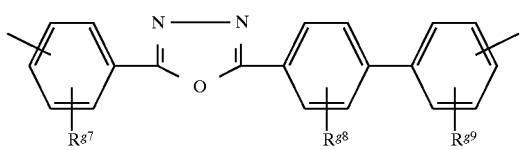

wherein $R^{g7}$, $R^{g8}$ and $R^{g9}$ are the same or different and indicate a hydrogen atom, an alkyl group having 1 to 5 carbon atoms, a halogen atom, an alkoxy group, an aryl group or an aralkyl group;

(CG5) Dithioketopyrrolopyrrole pigment

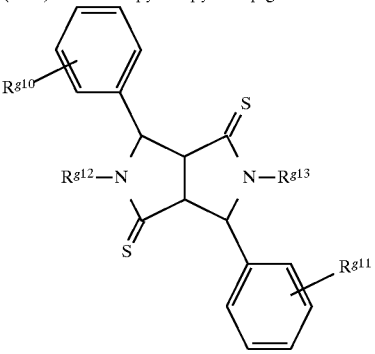
(CG5)

wherein $R^{g10}$ and $R^{g11}$ are the same or different and indicate a hydrogen atom, an alkyl group, an alkoxy group or a halogen atom; and $R^{g12}$ and $R^{g13}$ are the same or different and indicate a hydrogen atom, an alkyl group or an aryl group;

(CG6) Metal-free naphthalocyanine pigment
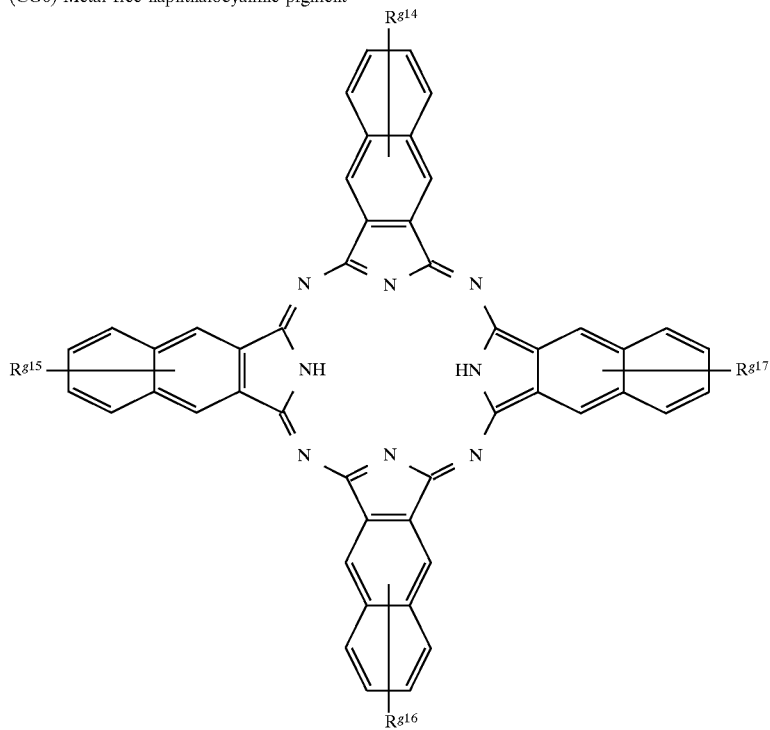
(CG6)
wherein $R^{g14}$, $R^{g15}$, $R^{g16}$ and $R^{g17}$ are the same or different and indicate a hydrogen atom, an alkyl group, an alkoxy group or a halogen atom;
(CG7) Metal naphthalocyanine pigment
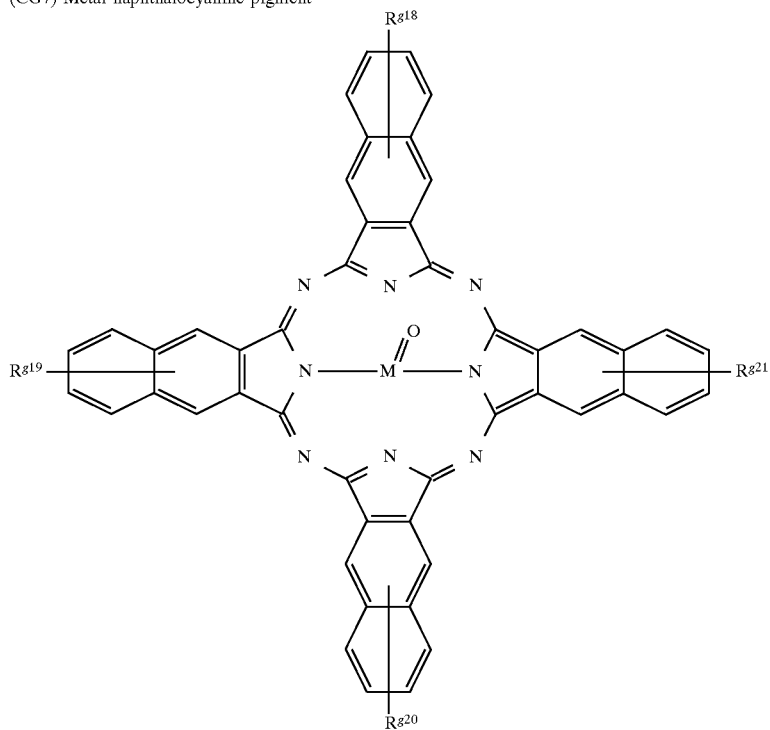
(CG7)

wherein $R^{g18}$, $R^{g19}$, $R^{g20}$ and $R^{g21}$ are the same or different and indicate a hydrogen atom, an alkyl group, an alkoxy group or a halogen atom; and M indicates Ti or V;

(CG8) Squaraine pigment

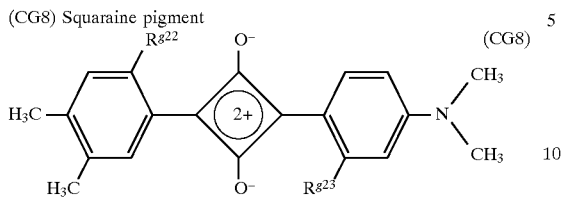

wherein $R^{g22}$ and $R^{g23}$ are the same or different and indicate a hydrogen atom, an alkyl group, an alkoxy group or a halogen atom;

(CG9) Trisazo pigment

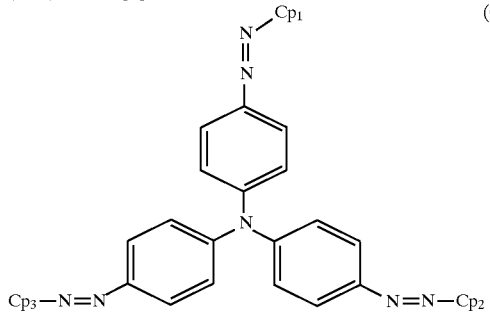

wherein $Cp_1$, $Cp_2$ and $Cp_3$ are the same or different and indicate a coupler residue;

(CG10) Indigo pigment

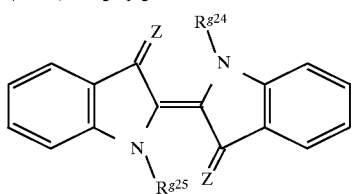

wherein $R^{g24}$ and $R^{g25}$ are the same or different and indicate a hydrogen atom, an alkyl group or an aryl group; and Z indicates an oxygen atom or a sulfur atom;

(CG11) Azulenium pigment

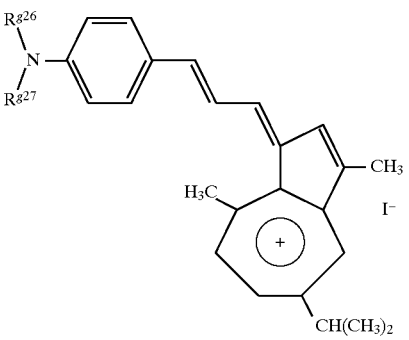

wherein $R^{g26}$ and $R^{g27}$ are the same or different an indicate a hydrogen atom, an alkyl group or an aryl group; and (CG12) Cyanine pigment wherein $R^{g28}$ and $R^{g29}$ are the same or different and indicate a hydrogen atom, an alkyl group, an alkoxy group or a halogen atom; and $R^{g30}$ and $R^{g31}$ are the same or different and indicate a hydrogen atom, an alkyl group or an aryl group.

In the aforementioned electric generating materials, examples of the alkyl group having not more than 18 carbon atoms include the aforementioned alkyl group having 1 to 6 carbon atoms, octyl, nonyl, decyl, dodecyl, tridecyl, pentadecyl and octadecyl.

Examples of the cycloalkyl group having 3 to 8 carbon atoms include the aforementioned cycloalkyl group having 3 to 6 carbon atoms, cycloheptyl and cyclooctyl. The alkoxy group, the aryl group and the aralkyl group include the same as mentioned above respectively.

Examples of the alkanoyl group include formyl, acetyl, propionyl, butyryl, pentanoyl, hexanoyl and the like.

Examples of the heterocyclic group include thienyl, pyrrolyl, pyrrolidinyl, oxazolyl, isooxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino and thiazolyl.

The above heterocyclic groups may be condensed with aromatic ring.

Examples of the substituent with which the above groups may be substituted include halogen atom, amino group, hydroxy group, carboxyl group which may be esterified, cyano group, alkyl group having 1 to 6 carbon atoms, alkoxy group having 1 to 6 carbon atoms, and alkenyl groups having 2 to 6 carbon atoms which may have aryl groups.

Examples of the coupler residue represented by $A^1$, $A^2$, and $C_{p1}$, $C_{p2}$, $C_{p3}$ include groups represented by the following general formulas (21) through (27):

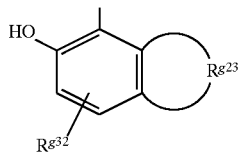
(21)

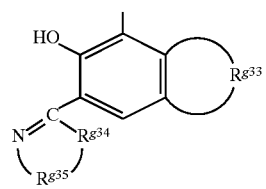
(22)

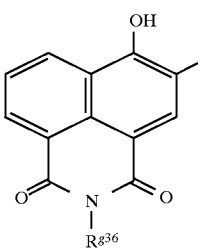
(23)

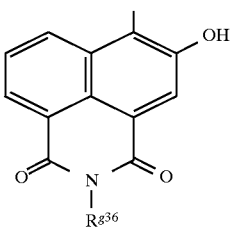
(24)

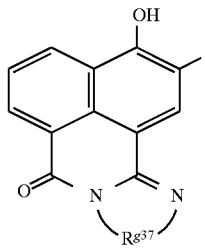
(25)

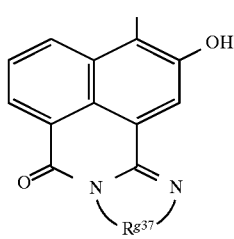
(26)

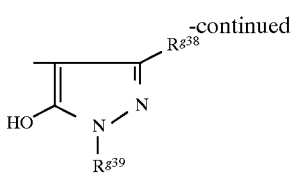
(27)

In the respective formulas, $R^{g32}$ indicates a carbamoyl group, a sulfamoyl group, an allophanoyl group, an oxamoyl group, an anthraniloyl group, a carbazoyl group, a glycyl group, a hydantoyl group, a phthalamoyl group or a succinamoyl group. These groups may contain a substituent, such as halogen atom, phenyl group which may have a substituent, naphthyl group which may have a substituent, nitro group, cyano group, alkyl group, alkenyl group, carbonyl group and carboxyl group.

$R^{g33}$ indicates an atomic group needed in forming an aromatic ring, polycyclic hydrocarbon or heterocyclic ring through condensation with benzene ring. These rings may have the same substituents as defined above.

$R^{g34}$ indicates an oxygen atom, a sulfur atom or an imino group.

$R^{g35}$ indicates a divalent chain hydrocarbon group or a divalent aromatic hydrocarbon group. These groups may have the same substituents as defined above.

$R^{g36}$ indicates an alkyl group, an aralkyl group, an aryl group or a heterocyclic group. These groups may have the same substituents as defined above.

$R^{g37}$ indicates a divalent chain hydrocarbon group, a divalent aromatic hydrocarbon group, or an atomic group needed in forming a heterocyclic ring together with a moiety of the following formula (28):

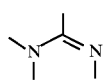
(28)

in the aforesaid general formulas (25) or (26).

These rings may have the same substituents as defined above.

$R^{g38}$ indicates a hydrogen atom, an alkyl group, an amino group, a carbamoyl group, a sufamoyl group, an allophanoyl group, a carboxyl group, an alkoxycarbonyl group, an aryl group or a cyano group. The groups except for hydrogen atom may have the substituents as defined above.

$R^{g39}$ indicates an alkyl group or an aryl group. These groups may have the same substituents as defined above.

Examples of the alkenyl group include alkenyl groups having 2 to 6 carbon atoms, such as vinyl, allyl, 2-butenyl, 3-butenyl, 1-methylallyl, 2-pentenyl and 2-hexenyl.

In the aforesaid $R^{g33}$, examples of the atomic group needed in forming the aromatic ring through condensation with the benzene ring, include alkylene groups having 1 to 4 carbon atoms, such as methylene, ethylene, trimethylene and tetramethylene.

Examples of the aromatic ring formed by the aforesaid condensation of $R^{g33}$ and the benzene ring include naphthalene ring, anthracene ring, phenanthrene ring, pyrene ring, chrysene ring and naphthacene ring.

In $R^{g33}$, examples of the atomic group needed in forming the polycyclic hydrocarbon through condensation with the benzene ring include the aforesaid alkylene group having 1 to 4 carbon atoms, a carbazole ring, a benzocarbazole ring and dibenzofuran ring.

Further in $R^{g33}$, examples of the atomic group required for forming the heterocyclic ring through condensation with the benzene ring include benzofuranyl, benzothiophenyl, indolyl, 1H-indolyl, benzoxazolyl, benzothiazolyl, 1H-indadolyl, benzoimidazolyl, chromenyl, chromanyl, isochromanyl, quinolinyl, isoquinolinyl, cinnolinyl, phthalazinyl, quinazonilyl, quinoxanilyl, dibenzofuranyl, carbazolyl, xanthenyl, acridinyl, phenanthridinyl, phenazinyl, phenoxazinyl and thianthrenyl.

Examples of the aromatic heterocyclic group formed by the aforesaid condensation of $R^{g33}$ and the benzene ring include thienyl, furyl, pyrrolyl, oxazolyl, isoxazolyl, thiazolyl, isothiazolyl, imidazolyl, pyrazolyl, triazolyl, tetrazolyl, pyridyl and thiazolyl. Examples of the above heterocyclic groups include heterocyclic group condensed with other aromatic ring, such as, benzofuranyl, benzoimidazolyl, benzoxazolyl, benzothiazolyl and quinolyl.

In the aforesaid $R^{g35}$ and $R^{g37}$, examples of the divalent chain hydrocarbon group include ethylene, trimethylene and tetramethylene. Examples of the divalent aromatic hydrocarbon group include phenylene, naphthylene and phenanthylene.

In the aforesaid $R^{g36}$ examples of the heterocyclic group include pyridyl, pyrazyl, thienyl, pyranyl, indolyl and the like.

In the aforesaid $R^{g37}$, examples of the atomic group needed in forming the heterocycle in combination with the portion represented by the aforesaid formula (28) include phenylene, naphthylene, phenanthyrene, ethylene, trimethylene and tetramethylene.

Examples of the aromatic heterocyclic group formed by the combination of the aforesaid $R^{g37}$ with the moiety represented by the aforesaid formula (28), include benzoimidazole, benzo[f]benzoimidazole, dibenzo[e,g]benzoimidazole, benzopyrimidine and the like. These groups may have the same substituents as defined above.

In the aforesaid $R^{g38}$, examples of the alkoxycarbonyl group include methoxycarbonyl, ethoxycarbonyl, propoxycarbonyl and butoxycarbonyl.

In addition to the electric charge generating materials exemplified as above, this invention may employ conventional electric charge generating materials such as selenium, selenium-tellurium, amorphous silicon, pyrylium salt, anthanthrone pigment, triphenylmethane pigment, threne pigment, toluidine pigment, pyrazoline pigment and quinacridon pigment.

The aforementioned electric charge generating materials may be used alone or in any combination thereof so as to present an absorption wavelength in a desired region. In this case, to reduce residual potential and to increase photosensitivity, it is desirable that the electric charge generating material has an ionization potential of from 4.8 to 6.0 eV, particularly from 5.0 to 5.8 eV, in order to balance with the hole transport material whose ionization potential is from 4.8 to 5.6 eV.

The most preferred electric charge generating material are phthalocyanine pigment and perylene pigment of the aforesaid general formula (CG3). Among the phthalocyanine pigment, preferred is an X-type metal-free phthalocyanine of the aforesaid general formula (CG1) and an oxotitanyl phthalocyanine of the aforesaid general formula (CG2). Among the perylene pigment, preferred is a compound represented by a general formula (CG3a):

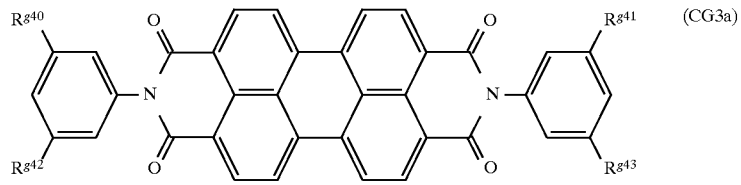

wherein $R^{g40}, R^{g41}, R^{42}$ and $R^{g43}$ are the same or different and indicate a hydrogen atom, an alkyl group, an alkoxy group or an aryl group.

In the above general formula (CG3a), examples of the alkyl group, alkoxy group and aryl group which correspond to the substituents $R^{g40}$ through $R^{g43}$, include the same as defined above respectively.

Of the electric charge generating materials, the phthalocyanine pigment is suitably used as the electric charge generating material for an electrophotosensitive material which presents its photosensitivity in the wavelength region of not less than 700 nm. That is, since the phthalocyanine pigment has superior matching with the tryptanthrine derivative (1) (electron transport material), electrophotosensitive material containing the both can present high photosensitivity in the above wavelength region. Accordingly, such an electrophotosensitive material is suitable for image forming apparatuses of digital optical system which employs a light source having the wavelength of not less than 700 nm.

The perylene pigment is also suitable for the electric charge generating material used in an electrophotosensitive material having the photosensitivity in the visible region. The perylene pigment of the formula (CG3a), in particular, is excellent in matching with the tryptanthrine derivative (1) (electron transport material). Thus, an electrophotosensitive material containing the both can present high photosensitivity in the visible region. Accordingly, such an electrophotosensitive material is suitable for image forming apparatuses of analog optical system which employs a light source having the wavelength in the visible region.

Resin Binder

As the resin binder to disperse the aforementioned ingredients, a variety of resins conventionally used for the organic photosensitive layer can be used. There are, for example, thermoplastic resins such as styrene polymer, styrene-butadiene copolymer, styrene-acrylonitrile copolymer, styrene-maleic acid copolymer, acrylic polymer, styrene-acrylic acid copolymer, polyethylene, ethylene-vinyl acetate copolymer, chlorinated polyethylene, polyvinyl chloride, polypropylene, ionomer, vinyl chloride-vinylacetate copolymer, polyester, alkyd resin, polyamide, polyurethane, polycarbonate, polyarylate, polysulfone, diarylphthalate resin, ketone resin, polyvinylbutyral resin, polyether resin and polyester resin; crosslinking thermoset resins such as silicone resin, epoxy resin, phenol resin, urea resin, melamine resin and the like; and photosetting resins such as epoxyacrylate, urethane acrylate and the like.

These resin binders may be used alone or in any combination thereof. Among those, preferred are styrene polymer, acrylic polymer, styrene-acrylic copolymer, polyester, alkyd resin, polycarbonate and polyarylate.

The process for preparing the electrophotosensitive material of this invention will be described.

The single-layer type electrophotosensitive material is formed by applying a coating solution to a conductive substrate by means of coating or the like, followed by drying the solution. The above coating solution is prepared by dissolving and dispersing, in a suitable solvent, a predetermined electron transport material together with the electric charge generating material, the hole transport material, the resin binder and the like.

In the single-layer type electrophotosensitive material, to 100 parts by weight of the resin, a proportion of the electric charge generating material is from 0.1 to 50 parts by weight, particularly from 0.5 to 30 parts by weight; that of the electron transport material is from 5 to 100 parts by weight, particularly from 10 to 80 parts by weight; and that of the hole transport material is from 5 to 500 parts by weight, particularly from 25 to 200 parts by weight. A total amount of the hole transport material and the electron transport material is preferably from 20 to 500 parts by weight, particularly from 30 to 200 parts by weight, per 100 parts by weight of the resin binder.

When an electron acceptive compound is added to the single-layer type photosensitive layer, its amount is preferably from 0.1 to 40 parts by weight, particularly from 0.5 to 20 parts per 100 parts by weight of the resin binder.

The thickness of the single-layer type photosensitive layer is from 5 to 100 μm, particularly from 10 to 50 μm.

The multi-layer type electrophotosensitive material is prepared by the steps of:

forming the electric charge generating layer containing the electric charge generating material on a conductive substrate by means of deposition or coating; and forming the electric charge transport layer on the resultant electric charge generating layer by applying thereto a coating solution containing the electron transport material and the resin binder by means of coating or the like, followed by drying.

In the multi-layer type electrophotosensitive material, the electric charge generating material and the resin binder composing the electric charge generating layer may be added in various proportions. But the electric charge generating material is preferably used in 5 to 1000 parts by weight, particularly 30 to 500 parts by weight, per 100 parts by weight of the resin binder.

When an electron acceptive compound is added to the electric charge generating layer, its amount is preferably from 0.1 to 40 parts by weight, particularly 0.5 to 20 parts by weight, per 100 parts by weight of the resin binder.

When an electron transport material is added to the electric charge generating layer, its amount is preferably from 0.5 to 50 parts by weight, particularly 1 to 40 parts by weight, per 100 parts by weight of the resin binder.

The electron transport material and the resin binder composing the electric charge transport layer may be used in various proportions as long as they do not inhibit the transport of electron or cause no crystallization. It is desirable that the electron transport material is used in 10 to 500 parts by weight, particularly 25 to 100 parts by weight, per 100 parts by weight of the resin binder, in order that the electric charge generated by light irradiation in the electric charge generating layer can be smoothly transported.

If an electron acceptive compound is added to the electric charge transport layer, its amount is from 0.1 to 40 parts by weight, particularly from 0.5 to 20 parts by weight, per 100 parts by weight of the resin binder.

As to the thickness of the multi-layer type photosensitive layer, the electric charge generating layer preferably has a thickness of about 0.01 to 5 μm, particularly about 0.1 to 3 μm, and the electric charge transport layer preferably has a thickness of about 2 to 100 μm, particularly about 5 to 50 μm.

As long as the characteristics of the electrophotosensitive material is not affected, there may be formed a barrier layer between the conductive substrate and photosensitive layer in the single-layer type electrophotosensitive material, and between the conductive substrate and the electric charge generating layer or the electric charge transport layer, or between the electric charge generating layer and the electric charge transport layer in the multi-layer type electrophotosensitive material.

Moreover, a protective layer may be formed on the surface of the electrophotosensitive material.

As long as the electrophotosensitive characteristics are not affected, the photosensitive layer of the single-layer type or the multi-layer type may contain a variety of known additives such as antideterioration agents (e.g., antioxidant, radical capturing agent, singlet quencher, ultraviolet absorber), softening agent, plasticizer, surfactant, extender, thickening agent, dispersion stabilizer, wax, acceptor, donor and the like.

To increase the photosensitivity of the electrophotosensitive material, there may be used known sensitizer such as terphenyl, halonaphthoquinone and acenaphthylene, together with the electric charge generating material.

Furthermore, the photosensitive layer may contain known electron transport material, in addition to the tryptanthrine derivative (1).

As such an electron transport material, there are, for example, a variety of known compounds having a high electron transport capability, the benzoquinone compounds of the general formula (EA1), the diphenoquinone compounds of the general formula (EA2), and compounds represented by the following formulas (ET1) through (ET13):

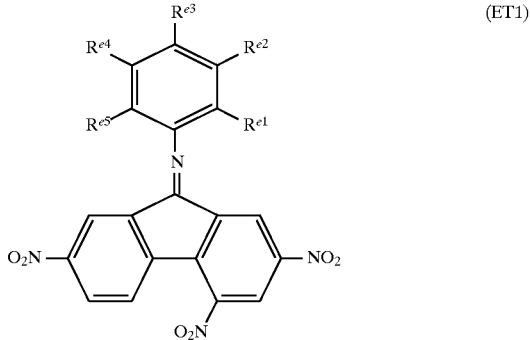

(ET1)

wherein $R^{e1}$, $R^{e2}$, $R^{e3}$, $R^{e4}$ and $R^{e5}$ are the same or different and indicate a hydrogen atom, an alkyl group which may have a substituent, an alkoxy group which may have a substituent, an aryl group which may have a substituent, an aralkyl group which may have a substituent, a phenoxy group which may have a substituent or a halogen atom.

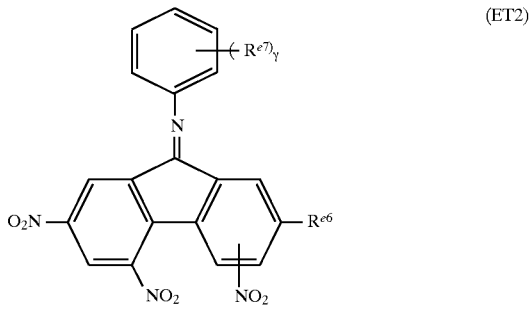

(ET2)

wherein $R^{e6}$ indicates an alkyl group and $R^{e7}$ indicates an alkyl group which may have a substituent, an alkoxy group which may have a substituent, an aryl group which may have a substituent, an aralkyl group which may have a substituent, a halogen atom or a halogenated alkyl group, and wherein γ indicates an integer of 0 to 5; and when γ is more than 2, each $R^{e7}$ may differ from one another.

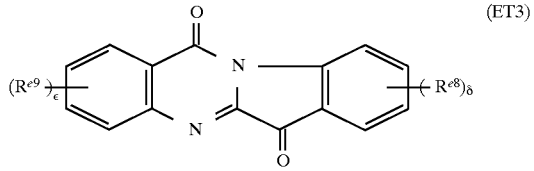

wherein $R^{e8}$ and $R^{e9}$ are the same or different and indicate an alkyl group; δ indicates an integer of 1 to 4; ε indicates an integer of 0 to 4; and when δ is more than 2, each $R^{e8}$ may differ from one another, and the same is ture for $R^{e9}$.

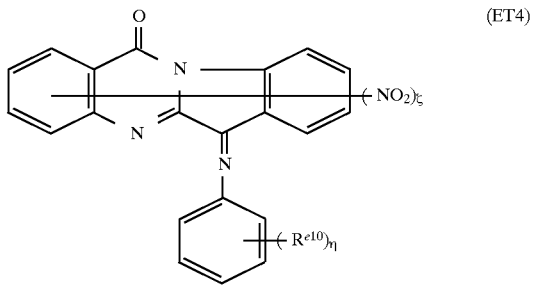

wherein $R^{e10}$ indicates an alkyl group, an aryl group, an aralkyl group, alkoxy group, a halogenated alkyl group or a halogen atom; and ζ indicates an integer of 0 to 4; η indicates an integer of 0 to 5; and when η is more than 2, each $R^{e10}$ may differ from one another.

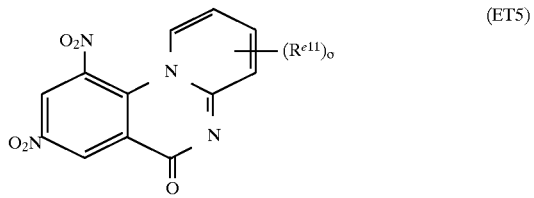

wherein $R^{e11}$ indicates an alkyl group; σ is an integer of 1 to 4; and when σ is more than 2, each $R^{e11}$ may differ from one another.

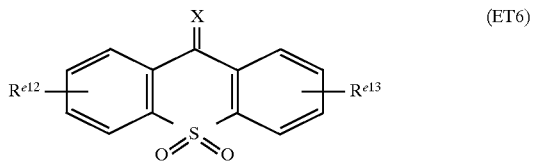

wherein $R^{e12}$ and $R^{e13}$ are the same or different and indicate a hydrogen atom, a halogen atom, an alkyl group, an aryl group, an aralkyloxycarbonyl group, an alkoxy group, a hydorxy group, a nitro group or a cyano group; and X indicates a group of oxygen atom, N—CN or $C(CN)_2$.

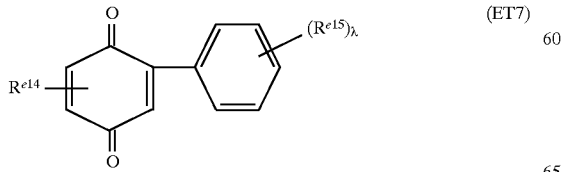

wherein $R^{e14}$ indicates a hydrogen atom, a halogen atom, an alkyl group or a phenyl group which may have a substituent;

$R^{e15}$ indicates a hydrogen atom, a halogen atom, an alkyl group which may have a substitutent, a phenyl group which may have a substituent, an alkoxycarbonyl group, an N-alkylcarbamoyl group, a cyano group or a nitro group; and λ indicates an integer of 1 to 3; and when λ is 2 or 3, each of $R^{e15}$ may differ from one another.

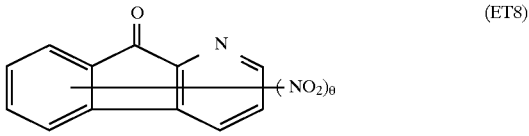

wherein θ is an integer of 1 or 2.

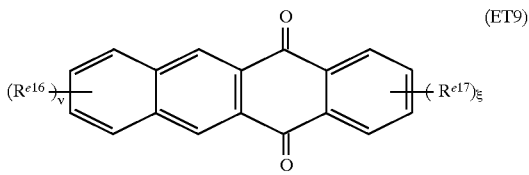

wherein $R^{e16}$ and $R^{e17}$ are the same or different and indicate a hydrogen atom, a halogen atom, an alkyl group which may have a substituent, a cyano group, a nitro group or an alkoxycarbonyl group; ν and ξ indicate an integer of 1 to 3; and when ν is 2 or 3, each $R^{e16}$ may differ from one another, and the same is true for $R^{e17}$.

wherein $R^{e18}$ and $R^{e19}$ are the same or different and indicate a phenyl group, a polycyclic aromatic group or a heterocyclic group. These groups may have a substituent.

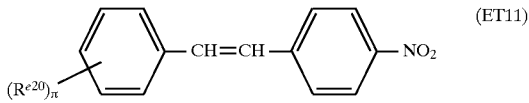

wherein $R^{e20}$ indicates an amino group, a dialkylamino group, an alkoxy group, an alkyl group or a phenyl group; π is an integer of 1 or 2; and when π is 2, each $R^{e20}$ may differ from each other.

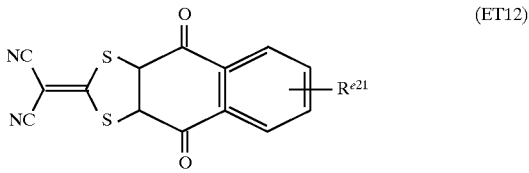

wherein $R^{e21}$ indicates a hydrogen atom, an alkyl group, an aryl group, an alkoxy group or an aralkyl group.

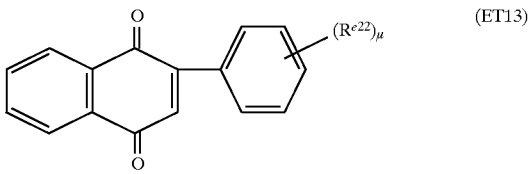

wherein $R^{e22}$ indicates a hydrogen atom, a halogen atom, an alkyl group which may have a substitutent, a phenyl group which may have a substituent, an alkoxycarbonyl group, an N-alkylcarbamoyl group, a cyano group or a nitro group; μ is an integer of 1 to 3; and when μ is 2 or 3, each $R^{e22}$ may differ from one another.

Examples of such electron transport material further include malononitril, thiopyran compound, tetracyanoethylene, include malononitril, thiopyran compound, tetracyanoethylene, 2,4,8-trinitrothioxanthone, dinitrobenzene, dinitroanthracene, dinitroacridine, nitroanthraquinone, dinitoranthraquinone, succinic anhydride, maleic anhydride and dibromomaleic anhydride.

In the aforementioned electron transport materials, examples of the alkyl group, the alkoxy group, the aryl group, the aralkyl group and halogen atom are the same as defined above respectively.

Examples of the halogenated alkyl group include halogenated alkyl groups wherein the moiety of the alkyl group has 1 to 6 carbon atoms, such as chloromethyl, bromomethyl, fluoromethyl, iodomethyl, 2-chloroethyl, 1-fluoroethyl, 3-chloropropyl, 2-bromopropyl, 1-chloropropyl, 2-chloro-1-methylethyl, 1-bromo-1-methylethyl, 4-iodobutyl, 3-fluorobutyl, 3-chloro-2-methylpropyl, 2-iodo-2-methylpropyl,1-fluoro-2-methylpropyl, 2-chloro-1,1-dimethylethyl, 2-bromo-1,1-dimethylethyl, 5-bromopentyl and 4-chlorohexyl.

Examples of the aromatic polycyclic group include naphthyl, phenanthryl and anthryl.

Examples of the heterocyclic group include thienyl, pyrrolyl, pyrrolidinyl, oxazolyl, isooxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino and thiazolyl. The above heterocyclic groups may be condensed with an aromatic ring.

Examples of the substituent with which the aforesaid groups may be substituted, include halogen atom, amino group, hydroxy group, carboxyl group which may be esterified, cyano group, alkyl group having 1 to 6 carbon atoms, alkoxy group having 1 to 6 carbon atoms, alkenyl group having 2 to 6 carbon atoms which may have an aryl group.

As the conductive substrate used in the electrophotosensitive material of this invention, a variety of materials having conductivity can be used. There are, for example, single metal such as aluminum, iron, copper, tin, platinum, silver, vanadium, molybdenum, chromium, cadmium, titanium, nickel, palladium, indium, stainless steel, brass and the like; plastic material with the aforesaid metals deposited or laminated thereon; and glasses coated with aluminum oxide, tin oxide, indium oxide or the like.

The conductive substrate may be in any form of sheet, drum and the like. It is necessary that the conductive substrate or the surface thereof is conductive. It is desirable that the conductive substrate presents sufficient mechanical strength during its use.

The electrophotosensitive layer of this invention is formed by applying a coating solution, which is prepared by dissolving or dispersing a resin component containing the aforementioned ingredients in a suitable solvent, to the conductive substrate, followed by drying the coating solution.

Specifically, the coating solution is prepared by dispersing and mixing the aforementioned electric charge generating material, the electric charge transport material, the resin binder and the like in a suitable solvent by a known method, such as roll mill, ball mill, atriter, paint shaker, supersonic dispenser or the like. Then, the resultant coating solution is applied to the substrate by a known method and then dried.

A variety of organic solvents are usable as the solvent for forming the coating solution. There are, for example, alcohols such as methanol, ethanol, isopropanol, butanol and the like; aliphatic hydrocarbons such as n-hexane, octane and cyclohexane; aromatic hydrocarbons such as benzene, toluene and xylene; halogenated hydrocarbons such as dichloromethane, dichloroethane, carbon tetrachloride and chlorobenzene; ethers such as dimethylether, diethylether, tetrahydrofuran, ethyleneglycol dimethylether and diethyleneglycol dimethylether; ketones such as acetone, methylethylketone and cyclohexanone; esters such as ethyl acetate, methyl acetate and the like; dimethylformaldehyde; dimethylformamide; dimethylsulfoxide, among others. These solvents may be used alone or in any combination thereof.

Additionally, there may be used a surfactant, a levelling agent or the like to increase the dispersibility of the electric charge transport material and the electric charge generating material and to improve the smoothness of the surface of the electrophotosensitive layer.

As described above, the tryptanthrine derivative (1) of this invention has superior electron transport capability, and therefore, the electrophotosensitive material which contains the derivative (1), as the electron transport material, has high photosensitivity. Accordingly, by the use of the electrophotosensitive material of this invention, it is possible to realize speeding-up in image forming apparatuses such as an electrostatic copying machines and the like.

EXAMPLE

The present invention will be described in detail by way of the examples thereof.

Tryptoanthorine Derivative

Synthesis Example 1

A 0.67 g (4.1 millimol) of isato acid anhydride represented by the following formula:

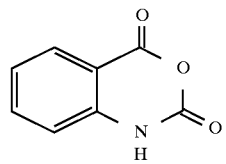
(1a-1)

1.0 g (4.4 millimol) of 5-bromoisatine represented by the following formula:

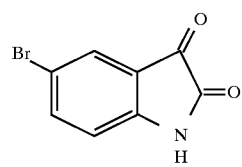
(1b-1)

and 20 ml of pyridine were heated under reflux for 6 hours in a 200 ml eggplant type flask to be reacted. After the reaction solution was cooled, a solid matter precipitated in the reaction solution was filtered off to give 0.40 g (yield: 31.0%) of 6-bromotryptanthrine represented by the following formula:

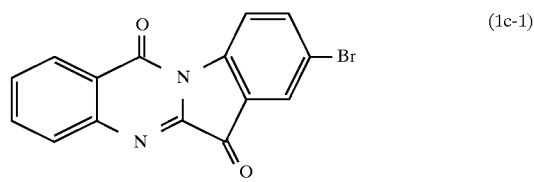
(1c-1)

A 1.5 g (4.5 millimol) of the 6-bormotryptanthrine, 0.64 g (7.2 millimol) of copper cyanide and 10 ml of N-methylpyrrolidone were heated under reflux for 4 hours in a 100 ml eggplant type flask to be reacted.

After the reaction, the reaction solution was poured into ice to allow a solid matter to deposit, which was filtered off. The resultant solid matter was dissolved in 20% aqueous ammonia, and the solution was extracted with chloroform.

The chloroform phase (organic phase) was separated from water phase. The separated organic phase was washed with water, neutralized and dried with magnesium sulfate anhydride, and the chloroform was distilled off to give a crystal. The resultant crystal was purified by subjecting to silica gel column chromatography and thus was obtained 0.76 g (yield: 62.0%) of a compound represented by the following formula:

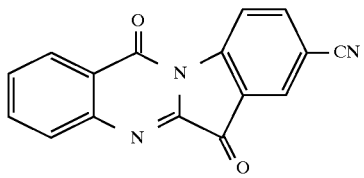
(11-1)

The melting point of the objective product is from 270° to 273° C. and the results of the elemental analysis are shown below.

| Elemental analysis | C | H | N |
|---|---|---|---|
| Calcd. (%) | 68.97 | 2.68 | 16.09 |
| Found (%) | 69.25 | 2.75 | 16.07 |

Figure 2:
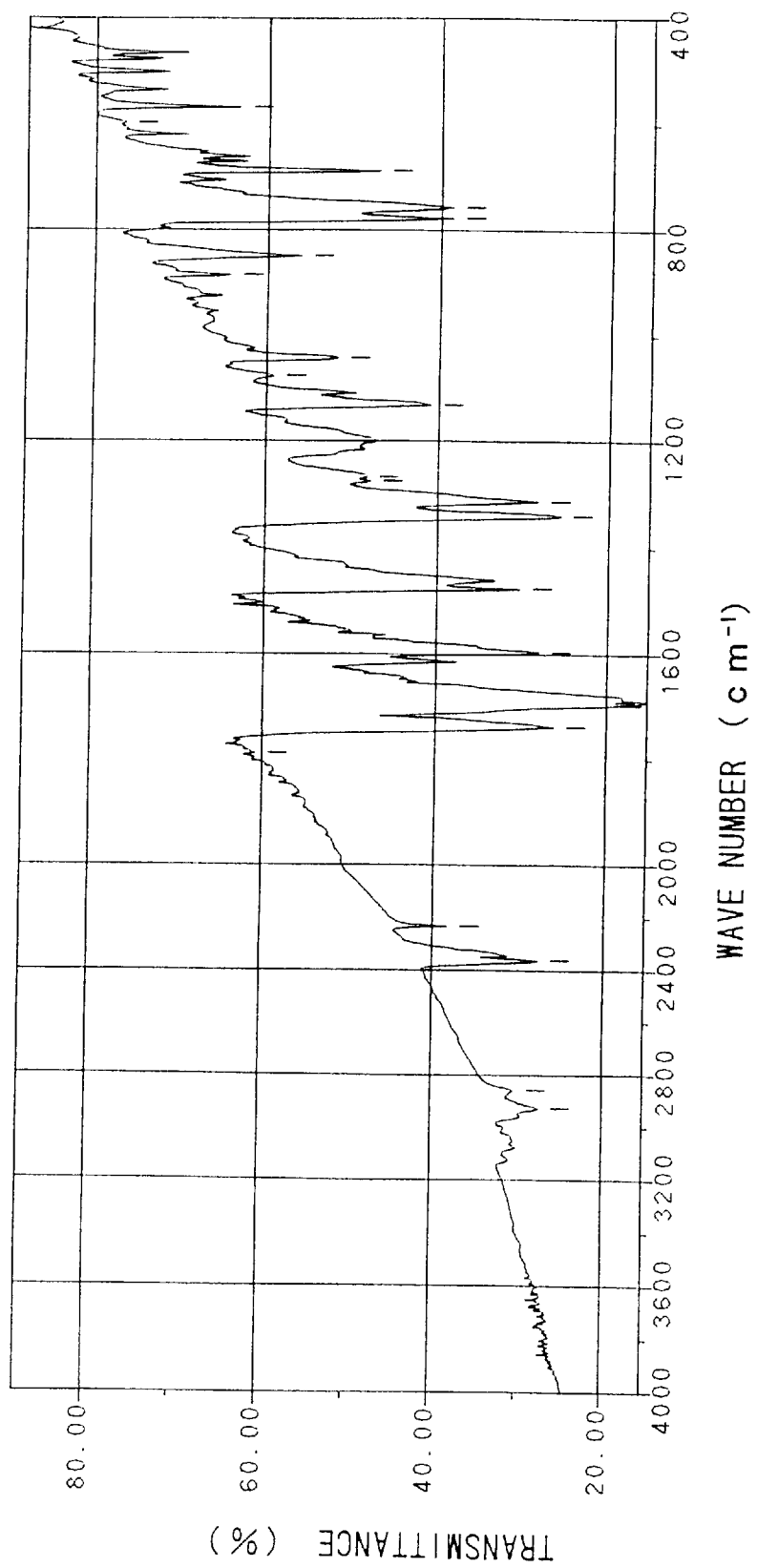
FIG. 2 is an illustration of infrared absorption spectrum of a compound obtained in Synthesis Example 1.

The results of the infrared spectroscopic analysis of the above product are shown in FIG. 2.

Synthesis Example 2

11 g (0.068 mol) of the isato acid anhydride of the aforesaid formula (1a1), and 12.9 g (0.068 mol) of 5-isopropylisatine represented by the following formula:

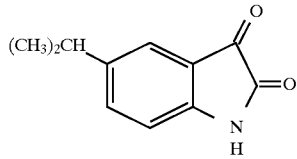
(1d-1)

and 20 ml of pyridine were heated under reflux for 6 hours in a 200 ml eggplant type flask to be reacted. After the reaction solution was cooled, a crystal precipitated in the reaction solution was filtered off to give 8.3 g (yield: 42%) of 6-isopropyltryptanthrine represented by the following formula:

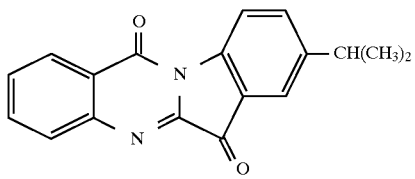
(1e-1)

A 5.0 g (0.017 mol) of the 6-isopropyltryptanthrine was dispersed in 80 ml of methylene chloride. 7.6 g (0.039 mol) of titanium tetrachloride was added and then 10 ml of methylene chloride solution containing 8.9 g (0.048 mol) of bistrimethylsilylcarbodiimido was added dropwise to the dispersion solution. The resultant mixture was stirred through the night at room temperature under an argon atmosphere for reaction.

After the reaction, the reaction solution was added in water, and the solution extracted with chloroform. The chloroform phase (organic phase) was separated from water phase. The separated organic phase was washed with water and dried with sodium sulfate anhydride. After the chloroform was distilled off, the resultant product was purified by subjecting to flash column chromatography (developing solvent: chloroform) to give 2.80 g (yield: 52.3%) of a compound of an orange solid matter represented by the following formula:

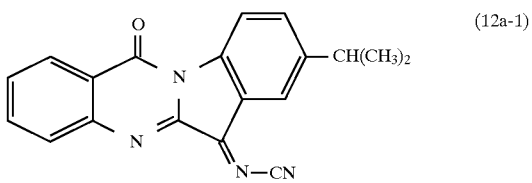
(12a-1)

The melting point of the objective product is 245° C. and the results of the elemental analysis are shown below.

| Elemental analysis | C | H | N |
|---|---|---|---|
| Calcd. (%) | 72.61 | 4.46 | 17.83 |
| Found (%) | 73.25 | 4.50 | 17.95 |

Figure 3:
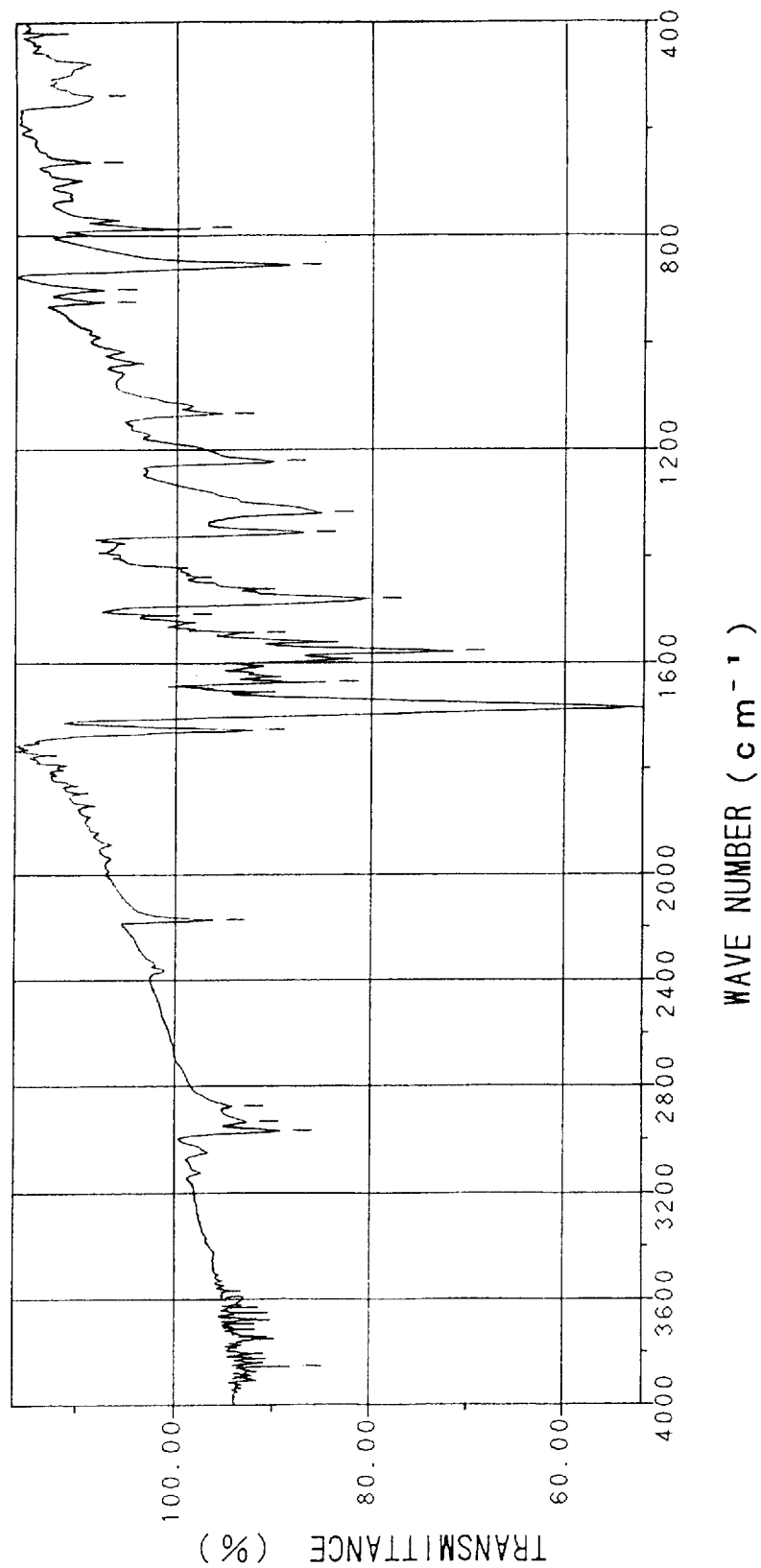
FIG. 3 is an illustration of infrared absorption spectrum of a compound obtained in Synthesis Example 2.

The results of the infrared spectroscopic analysis of the above product are shown in FIG. 3.

Synthesis Example 3

11 g (0.068 mol) of the isato acid anhydride of the aforesaid formula (1a-1), and 10 g (0.068 mol) of isatine represented by the following formula:

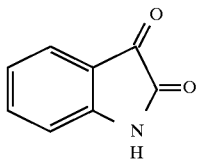
(1d-2)

and 20 ml of pyridine were heated under reflux for 6 hours in a 200 ml eggplant type flask to be reacted. After the reaction solution was cooled, a crystal precipitated in the reaction solution was filtered off to give 6.46 g (yield: 38%) of tryptanthrine represented by the following formula.

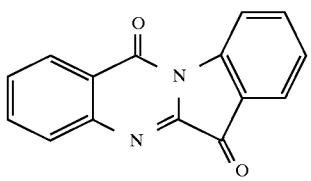
(1e-2)

A 5.0 g (0.02 mol) of the tryptanthrine together with 1.0 g of sodium ethoxide were added in 100 ml of ethanol to be stirred at room temperature.

Then, a solution containing 2.1 g (0.032 mol) of malononitrile dissolved in 50 ml of ethanol was added in this solution to be stirred at 40° to 50° C. for one hour to be reacted. The reaction solution was poured into water, and three-time extraction of the solution with chloroform were carried out. The chloroform phase (organic phase) was separated from water phase. The separated organic phase was washed with water and dried with magnesium sulfate anhydride, the solvent was distilled off to give a crystal. The resultant crystal was purified by subjecting to silica gel column chromatography to thereby give 5.0 g (yield: 85.1%) of a red compound represented by the following formula:

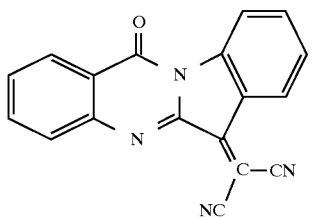
(13-1)

The melting point of the objective product is 213° to 215° C. and the results of the elemental analysis are shown below.

| Elemental analysis | C | H | N |
|---|---|---|---|
| Calcd. (%) | 72.97 | 2.70 | 18.92 |
| Found (%) | 73.32 | 2.75 | 18.64 |

Figure 4:
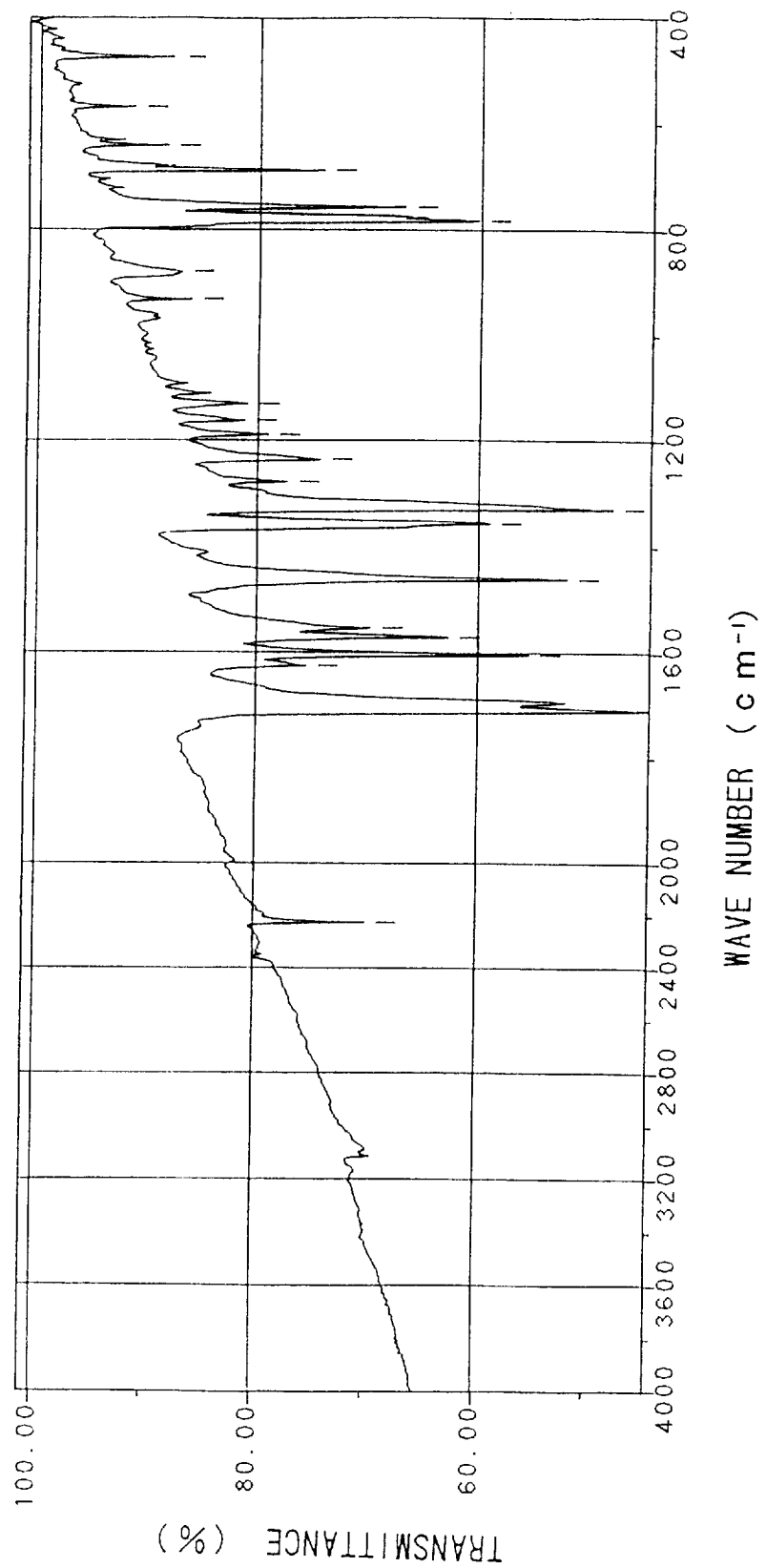
FIG. 4 is an illustration of infrared absorption spectrum of a compound obtained in Synthesis Example 3.

The results of the infrared spectroscopic analysis of the above product are shown in FIG. 4.

Synthesis Example 4

0.17 G (7 millimol) of sodium hydride and 7 ml of dried tetrahydrofuran were poured into a 100 ml two-necked flask to be stirred under stream of argon gas. A solution containing 1.56 g (7 millimol) of a diethyl phosphonate derivative represented by the following formula dissolved in 10 ml of tetrahydrofuran was added dropwise thereto and was stirred at room temperature for 3 hours:

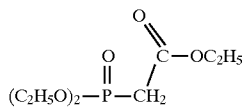
(1f-1)

Then, a solution containing 0.99 g (3.4 millimol) of the 6-isopropyltryptanthrine given by Synthesis Example 2 which is dissolved in 5 ml of tetrahydrofuran was added dropwise to this solution and was further stirred for reaction at room temperature for 3 hours.

After the reaction, the reaction solution was put into ice water, and the solution was extracted with chloroform. The chloroform phase (organic phase) was separated from water phase. The separated organic phase was washed and the chloroform was distilled off, the residue was purified by subjecting to silica gel column chromatography (developing solvent: chloroform) to give 0.43 g (yield: 35.0%) of a compound represented by the following formula:

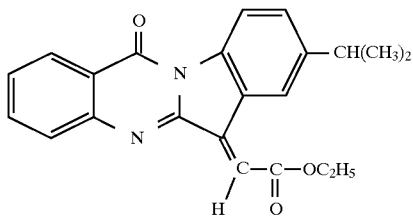
(13-2)

The melting point of the objective product is 205° to 207° C. and the results of the elemental analysis are shown below.

| Elemental analysis | C | H | N |
|---|---|---|---|
| Calcd. (%) | 73.32 | 5.59 | 7.77 |
| Found (%) | 73.40 | 5.51 | 7.81 |

Figure 5:
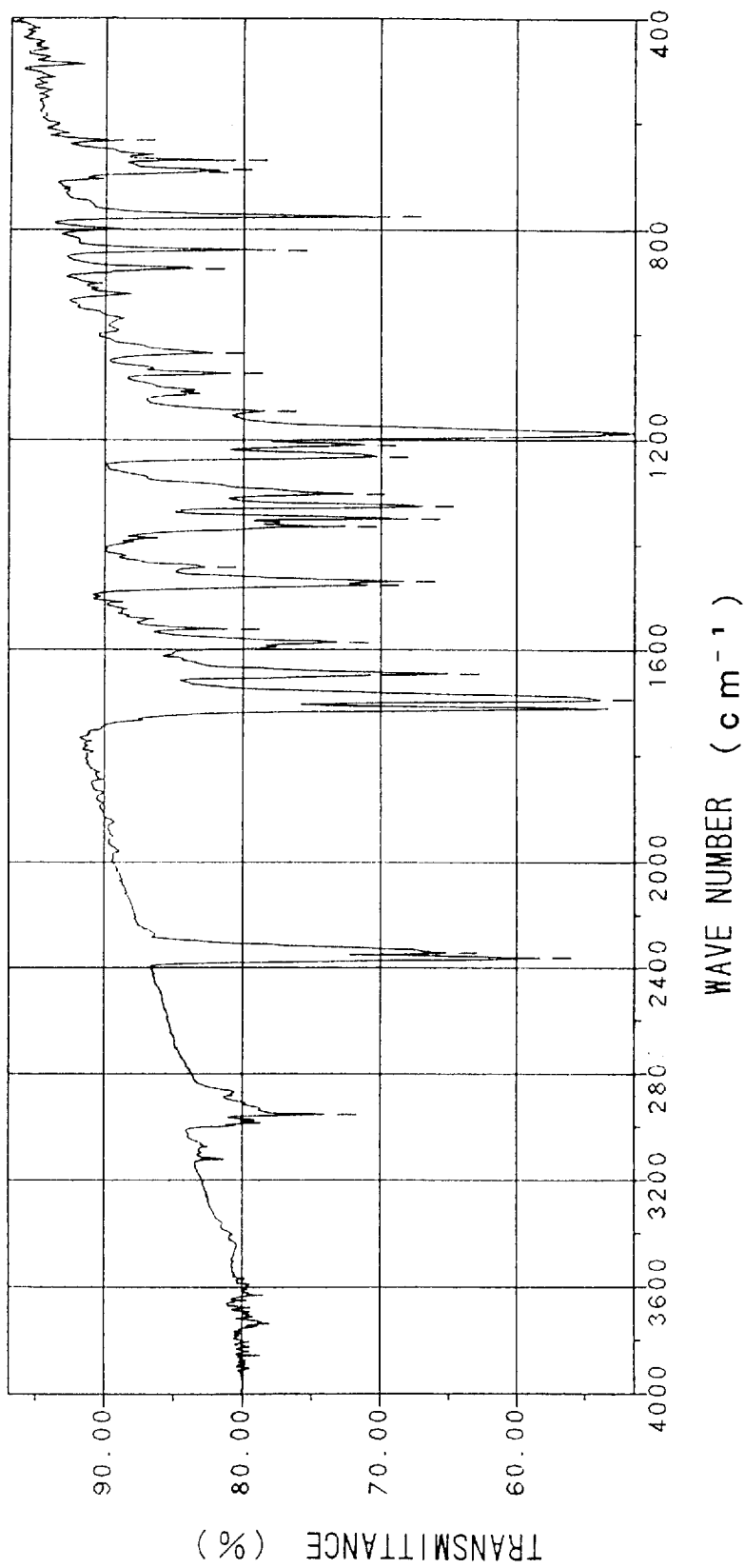
FIG. 5 is an illustration of infrared absorption spectrum of a compound obtained in Synthesis Example 4.

The results of the infrared spectroscopic analysis of the above product are shown in FIG. 5.

Synthesis Example 5

In the same manner as Synthesis Example 4, except that in stead of the compound of the formula (1f-1), there was used 1.67 g (7 millimol) of a diethylphosphonate derivative represented by the following formula:

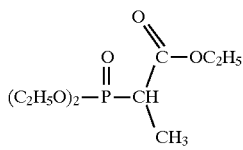
(1f-2)

to obtain 0.56 g(yield: 44.0%) of a compound represented by the following formula:

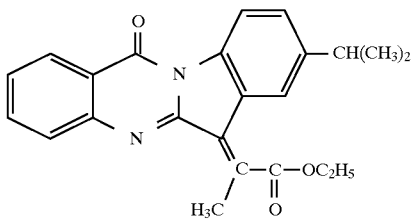
(13-3)

The melting point of the objective product was 200° to 201° C., and the results of the elemental analysis are shown below.

| Elernental analysis | C | H | N |
|---|---|---|---|
| Calcd. (%) | 73.78 | 5.92 | 7.48 |
| Found (%) | 73.85 | 5.89 | 7.53 |

Figure 6:
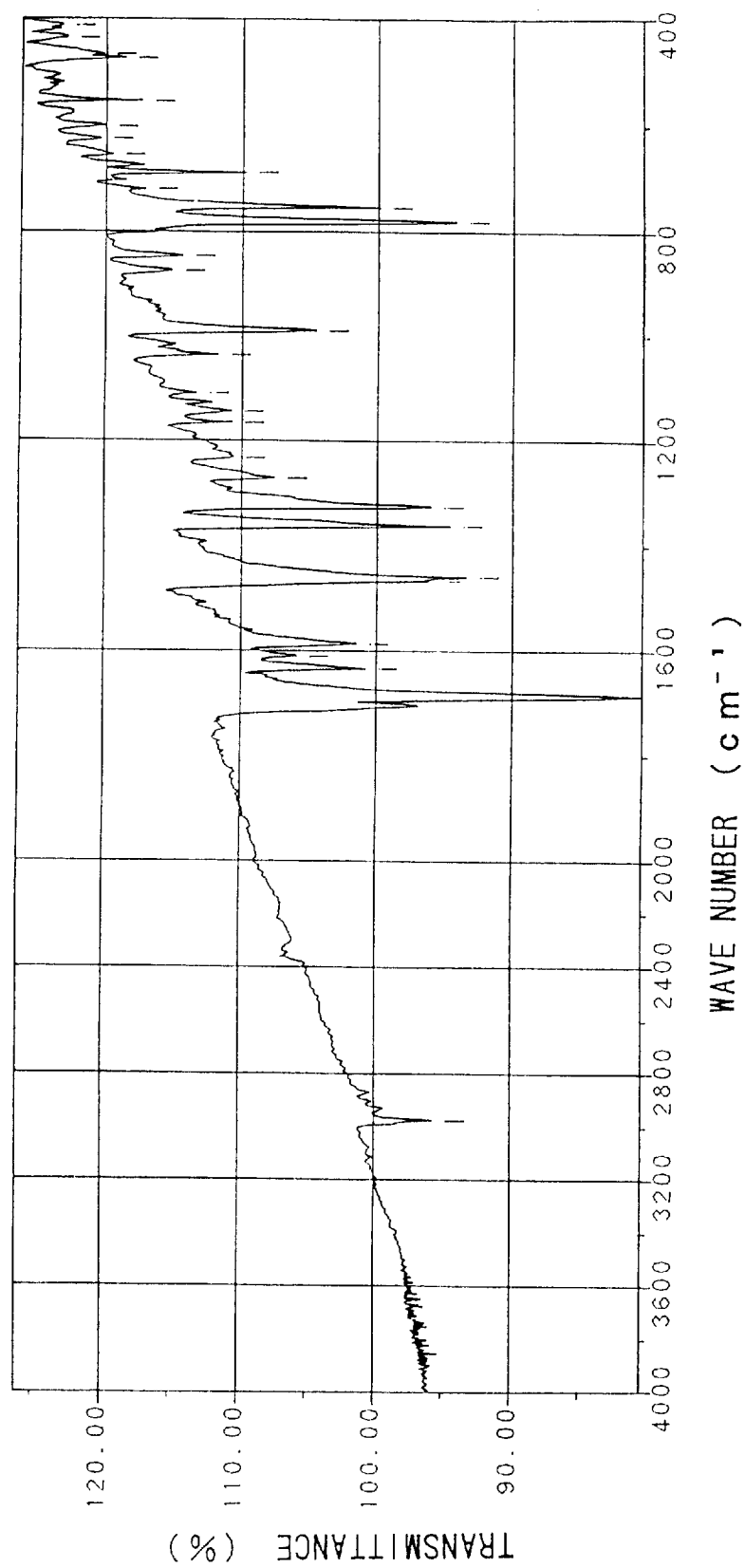
FIG. 6 is an illustration of infrared absorption spectrum of a compound obtained in Synthesis Example 5.

The results of the infrared spectroscopic analysis of the above product are shown in FIG. 6.

Electrophotosensitive Material for Digital Light Source (Single-layer Type) Example 1

5 Parts by weight of X-type metal-free phthalocyanine (Ip=5.38 eV) of the formula (CG1) as the electric charge generating material, 30 parts by weight of the compound of the formula (11-1) given by Synthesis Example 1 as the electron transport material, 50 parts by weight of N,N,N', N'-tetrakis(p-methylphenyl)-3,3'-dimethylbenzidine (Ip= 5.56 eV) of the formula (HT1-1) as the hole transport material, and polycarbonate as the resin binder were mixed and dispersed with 800 parts by weight of tetrahydrofuran using a ball mill for 50 hours to prepare a coating solution for single-layer type photosensitive layer.

This coating solution was applied on an aluminum tube as the conductive substrate by a dip coating method, followed by hot-air drying at 100° C. for 60 minutes to form an electrophotosensitive material for digital light source which has a single-layer type photosensitive layer of 15 to 20 μm in thickness.

Example 2

An electrophotosensitive material for digital light source having a single-layer type photosensitive layer was formed in the same manner as Example 1, except for that 5 parts by weight of oxotitanil phthalocyanine (Ip=5.32 eV) of the formula (CG2), as the electric charge generating material, was used instead of X-type metal-free phthalocyanine,.

Comparative Examples 1 and 2

An electrophotosensitive material for digital light source having a single-layer type photosensitive layer was formed in the same manner as Examples 1 and 2, except for that 30 parts by weight of 3,5-dimethyl-3',5'-di t-butyl-4,4'-diphenoquinone of the formula (EA2-1), as the electron transport material, was used instead of the compound of formula of (11-1).

Comparative Example 3

An electrophotosensitive material for digital light source having a single-layer type photosensitive layer was formed in the same manner as Example 1, except for that the electron transport material was not used.

The following test was conducted as to the electrophotosensitive materials of the above Examples and Comparative Examples, and their characteristics were evaluated.

Photosensitivity Test (I)

By using a drum sensitivity tester available from GEN-TEC Co., a voltage was applied on the surface of the photosensitive materials of the respective Examples and Comparative Examples to charge the surface at +700 V.

Monochromatic light having a wavelength of 780 nm (half-width: 20 nm) and a light intensity of 16 μW/cm2 from white light of a halogen lamp as an exposure light source through a band-pass filter was irradiated (irradiation time: 80 msec.) on the surface of the electrophotosensitive materials thus charged. A surface potential at the time at which 330 msec. has passed since the beginning of exposure was measured as a potential after exposure $V_L(V)$. The smaller potential after exposure $V_L(V)$ shows that the photosensitivity of the electrophotosensitive material is increased.

The results are shown in Table 1.

TABLE 1

|  | C.G.M. | E.T.M. | H.T.M. | VL (V) |
| --- | --- | --- | --- | --- |
| Ex. 1 | CG1 | 11-1 | HT1-1 | 194 |
| EX. 2 | CG2 | 11-1 | HT1-1 | 207 |
| C. Ex. 1 | CG1 | EA2-1 | HT1-1 | 220 |
| C. Ex. 2 | CG2 | EA2-1 | HT1-1 | 242 |
| C. Ex. 3 | CG1 | — | HT1-1 | 478 |

Electrophotosensitive Material for Digital Light Source (Single-layer Type: In Combination with Electron Example 2

An electrophotosensitive material for digital light source having a single-layer type photosensitive layer was formed in the same manner as Example 1, except for that 10 parts by weight of p-benzoquinone (redox potential:–0.81 V) of the formula (EA1-1), which is an electron acceptive compound, was added.

Example 4

An electrophotosensitive material for digital light source having a single-layer type photosensitive layer was formed in the same manner as Example 3, except for that 10 parts by weight of 2,6-di-tert-butyl-p-benzoquinone (redox potential:–1.31 V) of the formula (EA1-2) as the electron acceptive compound was used instead of p-benzoquinone.

Example 5

An electrophotosensitive material for digital light source having a single-layer type photosensitive layer was formed in the same manner as Example 3, except for that 10 parts by weight of 3,5-dimethyl-3',5'-di-tert-butyl-4,4'-diphenoquinone (redox potential=–0.86 V) of the formula (EA2-1) as the electron acceptive compound was used instead of p-benzoquinone.

Example 6

An electrophotosensitive material for digital light source having a single-layer type photosensitive layer was formed in the same manner as Example 3, except for that 10 parts by weight of 3,5,3',5'-tetrakis(tert-butyl)-4,4'-diphenoquinone (redox potential=–0.94 V) of the formula (EA2-2) as the electron acceptive compound was used instead of p-benzoquinone.

The aforesaid photosensitivity test (I) was conducted as to the electrophotosensitive materials of the above Examples, and their characteristics were evaluated. The results are shown in Table 2.

TABLE 2

|  | C.G.M. | E.T.M. | E.A.C. | H.T.M. | VL (V) |
| --- | --- | --- | --- | --- | --- |
| Ex. 3 | CG1 | 11-1 | EA1-1 | HT1-1 | 149 |
| EX. 4 | CG1 | 11-1 | EA1-2 | HT1-1 | 140 |
| Ex. 5 | CG1 | 11-1 | EA2-1 | HT1-1 | 139 |
| Ex. 6 | CG1 | 11-1 | EA2-2 | HT1-1 | 137 |

Electrophotosensitive Material for Digital Light Source (Multi-layer Type)

Example 7

100 parts by weight of X-type metal-free phthalocyanine of the formula (CG1) as the electric charge generating material, and 100 parts by weight of poly(vinyl butyral) as the resin binder were mixed and dispersed with 2000 parts by weight of tetrahydrofuran using a ball mill for 50 hours to prepare a coating solution for electric charge generating layer.

This coating solution was applied on an aluminum tube as the conductive substrate by a dip coating method, followed by hot-air drying at 100° C. for 60 minutes to form an electric charge generating layer of 1 μm in thickness.

Then, 100 parts by weight of the compound of the formula (11-1) given by Synthesis Example 1, as the electron transport material, and 100 parts by weight of polycarbonate as the resin binder were mixed and dispersed with 800 parts by weight of toluene using a ball mill for 50 hours to prepare a coating solution for electric charge transport layer.

This coating solution was applied on the aforesaid electric charge generating layer by a dip coating method, followed by hot-air drying at 100° C. for 60 minutes to form an electric charge transport layer of 20 μm in thickness. Thus was prepared an electrophotosensitive material for digital light source which has a multi-layer type photosensitive layer.

Comparative Example 4

An electrophotosensitive material for digital light source having a multi-layer type photosensitive layer was formed in the same manner as Example 7, except for that 100 parts by weight of 3,5-dimethyl-3',5'-di-tert-butyl-4,4'-diphenoquinone of the formula (EA2-1) as the electron transport material was used instead of the compound of the formula (11-1).

The aforesaid photosensitivity test (I) was conducted as to the electrophotosensitive materials of the above Example and Comparative Example, and their characteristics were evaluated. The results are shown in Table 3.

TABLE 3

|  | C.G.M. | E.T.M. | VL (V) |
|---|---|---|---|
| Ex. 7 | CG1 | 11-1 | 304 |
| C. Ex. 4 | CG1 | EA2-1 | 346 |

Electrophotosensitive Material for Analog Light Source (Single-layer Type)

Example 8

An electrophotosensitive material for analog light source having a single-layer type photosensitive layer was formed in the same manner as Example 1, except for that instead of the X-type metal-free phthalocyanine, there was used, as the electric charge generating material, 5 parts by weight of a compound (Ip=5.50 eV) represented by the following formula (CG3a-1):

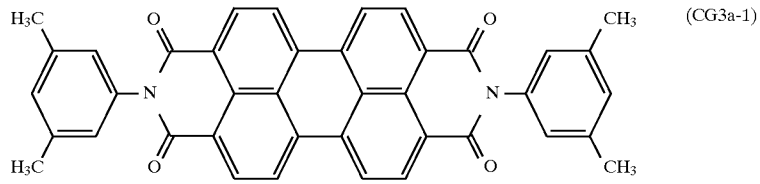

(CG3a-1)

Comparative Example 5

An electrophotosensitive material for analog light source having a single-layer type photosensitive layer was formed in the same manner as Example 8, except for that 30 parts by weight of 3,5-dimehtyl-3', 5'-di-tert-butyl-4,4'-diphenoquinone (EA2-1) as the electron transport material was used instead of the compound of the formula (11-1).

Comparative Example 6

An electrophotosensitive material for analog light source having a single-layer type photosensitive layer was formed in the same manner as Example 8, except for that the electron transport material was not used.

The following test was conducted as to the electrophotosensitive materials of the above Example and Comparative Examples, and their characteristics were evaluated.

Photosensitivity Test (II)

By using a drum sensitivity tester available from GENTEC Co., a voltage was applied on the surface of the photosensitive materials of the Example and Comparative Examples to charge the surface at +700 V, respectively.

White light (light intensity: 147 $\mu$W/cm$^2$) from a halogen lamp as an exposure light source was irradiated (irradiation time: 50 msec.) on the surface of the electropohtosensitive materials thus charged. A surface potential at the time at which 330 msec. has passed since the beginning of exposure was measured as a potential after exposure $V_L$(V). The smaller potential after exposure $V_L$(V) shows that the photosensitivity of the electrophotosensitive material is increased.

The results are shown in Table 4.

TABLE 4

|  | C.G.M. | E.T.M. | H.T.M. | VL (V) |
|---|---|---|---|---|
| Ex. 8 | CG3a-1 | 11-1 | HT1-1 | 247 |
| C. Ex. 5 | CG3a-1 | EA2-1 | HT1-1 | 294 |
| C. Ex. 6 | CG3a-1 | — | HT1-1 | 521 |

Electrophotosensitive Material for Analog Light Source (Multi-layer Type)

Example 9

An electrophotosensitive material for analog light source having a multi-layer type photosensitive layer was formed in the same manner as Example 7, except for that 100 parts by weight of the perylene pigment of the formula (CG3a-1) as the electric charge generating material was used instead of the X-type metal-free phthalocyanine.

Comparative Example 7

An electrophotosensitive material for analog light source having a multi-layer type photosensitive layer was formed in the same manner as Example 9, except for that 100 parts by weight of 3,5-dimethyl-3',5'-di-tert-butyl-4,4'-diphenoquinone of the formula (EA2-1) as the electron transport material was used instead of the compound of the formula (11-1).

The aforesaid photosensitivity Test (II) was conducted as to the electrophotosensitive materials of the above Example and Comparative Example, and their characteristics were evaluated. The results are shown in Table 5.

TABLE 5

|  | C.G.M. | E.T.M. | VL (V) |
|---|---|---|---|
| Ex. 9 | CG3a-1 | 11-1 | 330 |
| C. Ex. 7 | CG3a-1 | EA2-1 | 386 |

Electrophotosensitive Material for Digital Light Source (Single-layer Type)

Examples 10, 11

Electrophotosensitive materials for digital light source having a single-layer type photosensitive layer were formed in the same manner as Examples 1 and 2, except for that 30 parts by weight of the compound of the formula (12a-1) given by Synthesis Example 2, as the electron transport material, was used instead of the compound of the formula (11-1).

Examples 12 through 15

Electrophotosensitive materials for digital light source having a single-layer type photosensitive layer were formed in the same manner as Examples 3 through 6, except for that 30 parts by weight of the compound of the formula (12a-1) given by Synthesis Example 2, as the electron transport material, was used instead of the compound of the formula (11-1).

The aforesaid test (I) of the photosensitivity was conducted as to the electrophotosensitive materials of the above Examples, and their characteristics were evaluated. The results are shown in Table 6.

TABLE 6

|        | C.G.M. | E.T.M. | E.A.C. | H.T.M. | VL (V) |
|--------|--------|--------|--------|--------|--------|
| Ex. 10 | CG1    | 12a-1  | —      | HT1-1  | 210    |
| Ex. 11 | CG2    | 12a-1  | —      | HT1-1  | 221    |
| Ex. 12 | CG1    | 12a-1  | EA1-1  | HT1-1  | 203    |
| Ex. 13 | CG1    | 12a-1  | EA1-2  | HT1-1  | 197    |
| Ex. 14 | CG1    | 12a-1  | EA2-1  | HT1-1  | 196    |
| Ex. 15 | CG1    | 12a-1  | EA2-2  | HT1-1  | 192    |

Electrophotosensitive Material for Digital Light Source (Multi-layer Type)

Example 16

An electrophotosensitive material for digital light source having a multi-layer type photosensitive layer was formed in the same manner as Example 7, except for that 100 parts by weight of the compound of the formula (12a-1) given by Synthesis Example 2, as the electron transport material, was used instead of the compound of the formula (11-1).

The aforesaid Photosensitivity Test (I) was conducted as to the electrophotosensitive material of the above Example, and its characteristics were evaluated. The results are shown in Table 7.

TABLE 7

|        | C.G.M. | E.T.M. | VL (V) |
|--------|--------|--------|--------|
| Ex. 16 | CG1    | 12a-1  | 338    |

Electrophotosensitive Material for Analog Light Source (Single-layer Type)

Example 17

An electrophotosensitive material for analog light source having a single-layer type photosensitive layer was formed in the same manner as Example 8, except for that 30 parts by weight of the compound of the formula (12a-1) given by Synthesis Example 2, as the electron transport material, was used instead of the compound of the formula (11-1).

The aforesaid Photosensitivity Test (II) was conducted as to the electrophotosensitive material of the above Example, and its characteristics were evaluated. The results are shown in Table 8.

TABLE 8

|        | C.G.M. | E.T.M. | H.T.M. | VL (V) |
|--------|--------|--------|--------|--------|
| Ex. 17 | CG3a-1 | 12a-1  | HT1-1  | 262    |

Electrophotosensitive Material for Analog Light Source (Multi-layer Type)

Examples 18

An electrophotosensitive material for analog light source having a multi-layer type photosensitive layer was formed in the same manner as Example 9, except for that 100 parts by weight of the compound of the formula (12a-1) given by Synthesis Example 2, as the electron transport material, was used instead of the compound of the formula (11-1).

The aforesaid Photosensitivity Test (II) was conducted as to the electrophotosensitive material of the above Example, and its characteristics were evaluated. The results are shown in Table 9.

TABLE 9

|        | C.G.M. | E.T.M. | VL (V) |
|--------|--------|--------|--------|
| Ex. 18 | CG3a-1 | 12a-1  | 359    |

Electrophotosensitive Material for Digital Light Source (Single-layer Type)

Example 19, 20

Electrophotosensitive materials for digital light source having a single-layer type photosensitive layer were formed in the same manner as Examples 1 and 2, except for that 30 parts by weight of the compound of the formula (13-1) given by Synthesis Example 3, as the electron transport material, was used instead of the compound of the formula (11-1).

Examples 21, 22

Electrophotosensitive materials for digital light source having a single-layer type photosensitive layer were formed in the same manner as Examples 1 and 2, respectively, except for that 30 parts by weight of the compound of the formula (13-2) given by Synthesis Example 4, as the electron transport material, was used instead of the compound of the formula (11-1), respectively.

Examples 23, 24

Electrophotosensitive materials for digital light source having a single-layer type photosensitive layer were formed in the same manner as Examples 1 and 2, except for that 30 parts by weight of the compound of the formula (13-3) given by Synthesis Example 5, as the electron transport material, was used instead of the compound of the formula (11-1).

The aforesaid test (I) of the photosensitivity was conducted as to the electrophotosensitive materials of the above Examples, and their characteristics were evaluated. The results are shown in Table 10.

TABLE 10

|        | C.G.M. | E.T.M. | H.T.M. | VL (V) |
|--------|--------|--------|--------|--------|
| Ex. 19 | CG1    | 13-1   | HT1-1  | 195    |
| Ex. 20 | CG2    | 13-1   | HT1-1  | 205    |
| Ex. 21 | CG1    | 13-2   | HT1-1  | 203    |
| Ex. 22 | CG2    | 13-2   | HT1-1  | 220    |
| Ex. 23 | CG1    | 13-3   | HT1-1  | 205    |
| Ex. 24 | CG2    | 13-3   | HT1-1  | 230    |

Electrophotosensitive Material for Digital Light Source (Single-layer Type: In Combination with Electron Acceptable Compound)

Examples 25 through 28

Electrophotosensitive materials for digital light source having a single-layer type photosensitive layer were formed in the same manner as Examples 3 through 6, except for that 30 parts by weight of the compound of the formula (13-1)

given by Synthesis Example 3, as the electron transport material, was used instead of the compound of the formula (11-1).

Examples 29 through 32

Electrophotosensitive materials for digital light source having a single-layer type photosensitive layer were formed in the same manner as Examples 3 through 6, except for that 30 parts by weight of the compound of the formula (13-2) given by Synthesis Example 4, as the electron transport material, was used instead of the compound of the formula (11-1).

Examples 33 through 36

Electrophotosensitive materials for digital light source having a single-layer type photosensitive layer were formed in the same manner as Examples 3 through 6, except for that 30 parts by weight of the compound of the formula (13-3) given by Synthesis Example 5, as the electron transport material, was used instead of the compound of the formula (11-1).

The aforesaid Photosensitivity Test (I) was conducted as to the electrophotosensitive materials of the above Examples, and their characteristics were evaluated. The results are shown in Table 11.

TABLE 11

|  | C.G.M. | E.T.M. | E.A.C. | H.T.M. | VL (V) |
|---|---|---|---|---|---|
| Ex. 25 | CG1 | 13-1 | EA1-1 | HT1-1 | 167 |
| Ex. 26 | CG1 | 13-1 | EA1-2 | HT1-1 | 161 |
| Ex. 27 | CG1 | 13-1 | EA2-1 | HT1-1 | 158 |
| Ex. 28 | CG1 | 13-1 | EA2-2 | HT1-1 | 155 |
| Ex. 29 | CG1 | 13-2 | EA1-1 | HT1-1 | 195 |
| Ex. 30 | CG1 | 13-2 | EA1-2 | HT1-1 | 198 |
| EX. 31 | CG1 | 13-2 | EA2-1 | HT1-1 | 172 |
| Ex. 32 | CG1 | 13-2 | EA2-2 | HT1-1 | 167 |
| Ex. 33 | CG1 | 13-3 | EA1-1 | HT1-1 | 198 |
| Ex. 34 | CG1 | 13-3 | EA1-2 | HT1-1 | 202 |
| Ex. 35 | CG1 | 13-3 | EA2-1 | HT1-1 | 172 |
| Ex. 36 | CG1 | 13-3 | EA2-2 | HT1-1 | 170 |

Electrophotosensitive Material for Digital Light Source (Multi-layer Type)

Example 37

An electrophotosensitive material for digital light source having a multi-layer type photosensitive layer was formed in the same manner as Example 7, except for that 100 parts by weight of the compound of the formula (13-1) given by Synthesis Example 3, as the electron transport material, was used instead of the compound of the formula (11-1).

Example 38

An electrophotosensitive material for digital light source having a multi-layer type photosensitive layer was formed in the same manner as Example 7, except for that 100 parts by weight of the compound of the formula (13-2) given by Synthesis Example 4, as the electron transport material, was used instead of the compound of the formula (11-1).

Example 39

An electrophotosensitive material for digital light source having a multi-layer type photosensitive layer was formed in the same manner as Example 7, except for that 100 parts by weight of the compound of the formula (13-3) given by Synthesis Example 5, as the electron transport material, was used instead of the compound of the formula (11-1).

The aforesaid test (I) of the photosensitivity was conducted as to the electrophotosensitive materials of the above Examples, and their characteristics were evaluated. The results are shown in Table 12.

TABLE 12

|  | C.G.M. | E.T.M. | VL (V) |
|---|---|---|---|
| Ex. 37 | CG1 | 13-1 | 303 |
| Ex. 38 | CG1 | 13-2 | 308 |
| Ex. 39 | CG1 | 13-3 | 310 |

Electrophotosensitive Material for Analog Light Source (Single-layer Type)

Example 40

An electrophotosensitive material for analog light source having a single-layer type photosensitive layer was formed in the same manner as Example 8, except for that 30 parts by weight of the compound of the formula (13-1) given by Synthesis Example 3, as the electron transport material, was used instead of the compound of the formula (11-1).

Example 41

An electrophotosensitive material for analog light source having a single-layer type photosensitive layer was formed in the same manner as Example 8, except for that 30 parts by weight of the compound of the formula (13-2) given by Synthesis Example 4, as the electron transport material, was used instead of the compound of the formula (11-1).

Example 42

An electrophotosensitive material for analog light source having a single-layer type photosensitive layer was formed in the same manner as Example 8, except for that 30 parts by weight of the compound of the formula (13-3) given by Synthesis Example 5, as the electron transport material, was used instead of the compound of the formula (11-1).

The aforesaid Photosensitivity Test (II) was conducted as to the electrophotosensitive materials of the above Examples, and their characteristics were evaluated. The results are shown in Table 13.

TABLE 13

|  | C.G.M. | E.T.M. | H.T.M. | VL (V) |
|---|---|---|---|---|
| Ex. 40 | CG3a-1 | 13-1 | HT1-1 | 240 |
| Ex. 41 | CG3a-1 | 13-2 | HT1-1 | 230 |
| Ex. 42 | CG3a-1 | 13-3 | HT1-1 | 225 |

Electrophotosensitive Material for Analog Light Source (Multi-layer Type)

Example 43

An electrophotosensitive material for analog light source having a multi-layer type photosensitive layer was formed in the same manner as Example 9, except for that 100 parts by weight of the compound of the formula (13-1) given by Synthesis Example 3, as the electron transport material, was used instead of the compound of the formula (11-1).

Example 44

An electrophotosensitive material for analog light source having a multi-layer type photosensitive layer was formed in the same manner as Example 9, except for that 100 parts by weight of the compound of the formula (13-2) given by Synthesis Example 4, as the electron transport material, was used instead of the compound of the formula (11-1).

Example 45

An electrophotosensitive material for analog light source having a multi-layer type photosensitive layer was formed in the same manner as Example 9, except for that 100 parts by weight of the compound of the formula (13-3) given by Synthesis Example 5, as the electron transport material, was used instead of the compound of the formula (11-1).

The aforesaid test (II) of the photosensitivity was conducted as to the electrophotosensitive materials of the above Examples, and their characteristics were evaluated. The results are shown in Table 14.

TABLE 14

| | C.G.M. | E.T.M. | VL (V) |
|---|---|---|---|
| Ex. 43 | CG3a-1 | 13-1 | 320 |
| Ex. 44 | CG3a-1 | 13-2 | 337 |
| Ex. 45 | CG3a-1 | 13-3 | 321 |

What is claimed is:

1. A tryptanthrine compound represented by the formula (1):

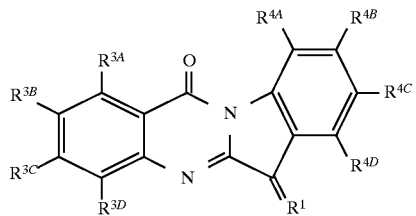

wherein $R^1$ is a group represented by the formula:

or a group represented by the formula:

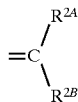

wherein $R^{2A}$ and $R^{2B}$ are the same or different and indicate a hydrogen atom, a cyano group, an acyl group which is a member selected from the group consisting of acetyl, propionyl, butyryl, isobutyryl, valeryl, isovaleryl, pivaloyl, benzoyl, 2-naphthoyl and o-toluoyl, an alkoxycarbonyl group where the alkoxy has 1 to 6 carbon atoms or an alkyl group having 1 to 6 carbon atoms, provided that $R^{2A}$ and $R^{2B}$ are not hydrogen atoms or cyano simultaneously;

where $R^1$ is the group of the formula (a) or of the formula (b), $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group from 1 to 6 carbon atoms which have a substituent selected from the group consisting of halogen, aryl, alkoxy from one to six carbons, and acyl where acyl has the same meaning as defined above.

2. A tryptanthrine compound according to claim 1, represented by the formula (12):

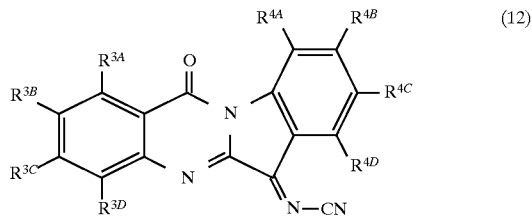

wherein $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group from 1 to 6 carbon atoms which may have a substituent.

3. A tryptanthrine compound according to claim 1, represented by the formula (13):

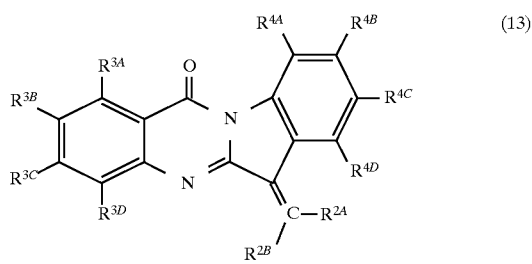

wherein $R^{2A}$ and $R^{2B}$ are the same or different and indicate a hydrogen atom, a cyano group, an acyl group which is a member selected from the group consisting of acetyl, propionyl, butyryl, isobutyryl, valeryl, isovaleryl, pivaloyl, benzoyl, 2-naphthoyl and o-toluoyl, an alkoxycarbonyl group where the alkoxy has 1 to 6 carbon atoms or an alkyl group having 1 to 6 carbon atoms, provided that $R^{2A}$ and $R^{2B}$ are not hydrogen atoms or cyano simultaneously, $R^{3A}$, $R^{3B}$, $R^{3C}$, $R^{3D}$, $R^{4A}$, $R^{4B}$, $R^{4C}$ and $R^{4D}$ are the same or different and indicate a hydrogen atom or an alkyl group from 1 to 6 carbon atoms which may have a substituent.

* * * * *